(12) United States Patent
Bak-Boychuk et al.

(10) Patent No.: US 10,376,681 B2
(45) Date of Patent: Aug. 13, 2019

(54) VACUUM-BASED COMPLIANCE RESTORATION

(71) Applicant: Edwards Lifesciences Corporation, Irvine, CA (US)

(72) Inventors: Gregory Bak-Boychuk, San Clemente, CA (US); Yaron Keidar, Irvine, CA (US); Bingquan Su, Los Angeles, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 292 days.

(21) Appl. No.: 15/335,054

(22) Filed: Oct. 26, 2016

(65) Prior Publication Data

US 2017/0246436 A1 Aug. 31, 2017

Related U.S. Application Data

(60) Provisional application No. 62/301,391, filed on Feb. 29, 2016.

(51) Int. Cl.
| | |
|---|---|
| *A61M 29/02* | (2006.01) |
| *A61M 25/10* | (2013.01) |
| *A61B 17/00* | (2006.01) |
| *A61M 25/04* | (2006.01) |
| *A61B 17/12* | (2006.01) |

(52) U.S. Cl.
CPC ....... *A61M 29/02* (2013.01); *A61B 17/00234* (2013.01); *A61B 17/12036* (2013.01); *A61B 17/12109* (2013.01); *A61B 17/12118* (2013.01); *A61B 17/12136* (2013.01); *A61B 17/12145* (2013.01); *A61M 25/04* (2013.01); *A61M 25/10186* (2013.11); *A61B 2017/00243* (2013.01); *A61M 2205/04* (2013.01)

(58) Field of Classification Search
CPC ........ A61B 17/00234; A61B 17/12036; A61B 17/12109; A61B 17/12118; A61B 17/12136; A61B 17/12145; A61B 2017/00243; A61M 2205/04; A61M 25/04; A61M 25/10186; A61M 29/02
See application file for complete search history.

(56) References Cited

U.S. PATENT DOCUMENTS

| | | | |
|---|---|---|---|
| 4,938,766 | A | 7/1990 | Jarvik |
| 7,766,814 | B2 | 8/2010 | Walsh |
| 8,876,850 | B1 | 11/2014 | Vollmers et al. |
| 9,017,359 | B2 | 4/2015 | Scandurra et al. |
| 9,039,725 | B1 | 5/2015 | Vollmers et al. |
| 2002/0091434 | A1 | 7/2002 | Chambers |

(Continued)

FOREIGN PATENT DOCUMENTS

WO 98/030269 A2 7/1998

OTHER PUBLICATIONS

Int'l. Search Report for PCT/US2016/059515, Completed Feb. 9, 2017.

*Primary Examiner* — Katherine M Shi

(57) ABSTRACT

A compliance restoration device includes a compliance balloon lumen, a chamber support structure disposed in the compliance balloon lumen and configured to expand to support an expanded volume of the compliance balloon lumen, and a spring assembly configured to cause the chamber support structure to expand by applying a force on a first end of the chamber support structure.

12 Claims, 18 Drawing Sheets

(56) References Cited

U.S. PATENT DOCUMENTS

| | | |
|---|---|---|
| 2004/0106971 A1 | 6/2004 | Schwartz et al. |
| 2007/0173924 A1 | 7/2007 | Gelbart et al. |
| 2010/0076548 A1 | 3/2010 | Konno |
| 2013/0079871 A1 | 3/2013 | Scandurra et al. |
| 2013/0245665 A1 | 9/2013 | Scandurra et al. |
| 2013/0261729 A1 | 10/2013 | Gillick et al. |
| 2014/0228878 A1 | 8/2014 | Scandurra et al. |
| 2015/0250991 A1* | 9/2015 | Silvestro ............... A61M 29/02 606/194 |
| 2015/0367113 A1 | 12/2015 | Vollmers et al. |

\* cited by examiner

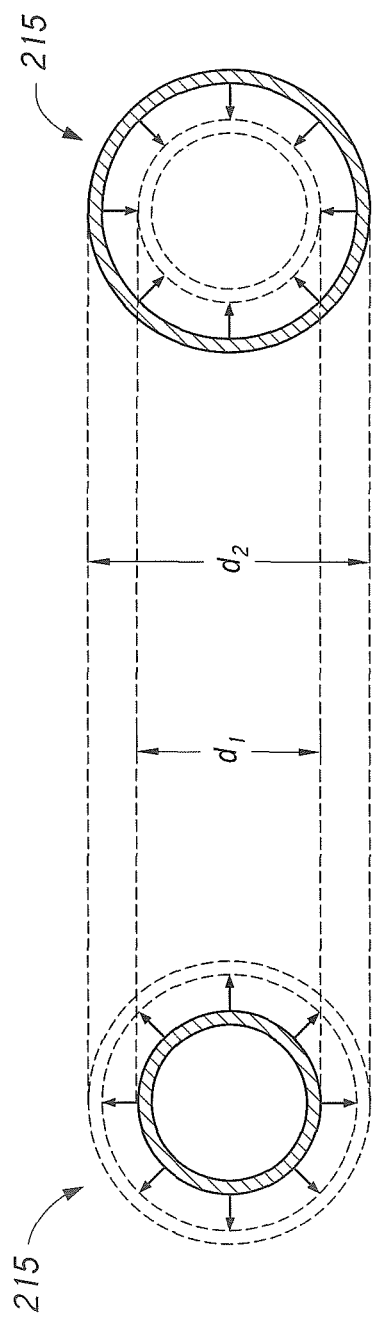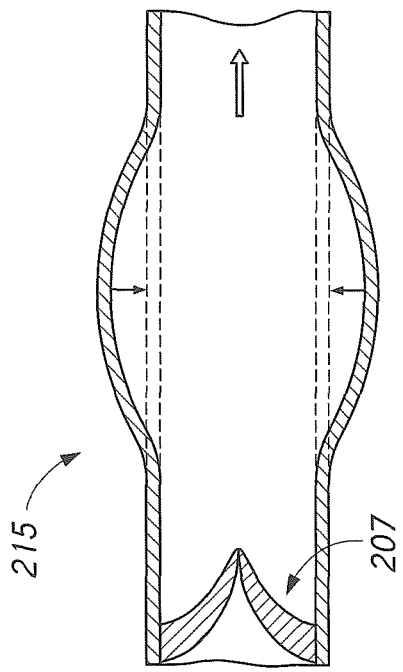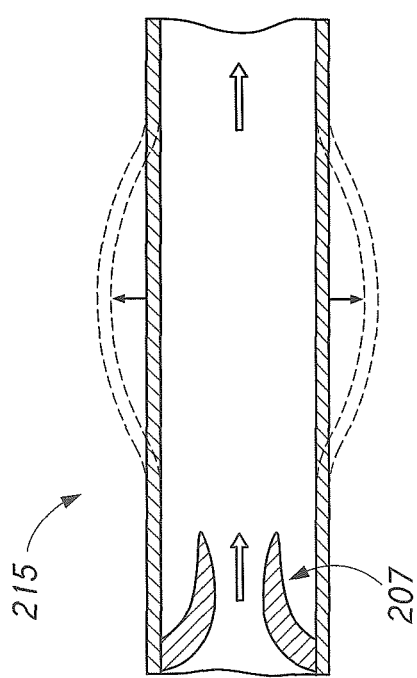
FIG. 2A
FIG. 2B
FIG. 3A
FIG. 3B

VACUUM-BASED COMPLIANCE RESTORATION

RELATED APPLICATION

This application claims priority to U.S. Provisional Application No. 62/301,391, filed on Feb. 29, 2016, entitled IMPLANTABLE VACUUM BASED COMPLIANCE BALLOON, the disclosure of which is hereby incorporated by reference in its entirety.

BACKGROUND

Field

The present disclosure generally relates to the field of heart failure treatment devices and methods.

Description of Related Art

Compliance of certain blood vessels in the human vasculature, such as arteries, may have an effect on various aspects of patient health. Compliance-restoration devices and methods can be utilized to improve certain aspects of patient health in some patients.

SUMMARY

In some implementations, the present disclosure relates to a compliance restoration device comprising a compliance balloon lumen, a chamber support structure disposed in the compliance balloon lumen and configured to expand to support an expanded volume of the compliance balloon lumen, and a spring assembly configured to cause the chamber support structure to expand by applying a force on a first end of the chamber support structure. The chamber support structure may comprise a wire mesh form configured to expand outward when a distance between first and second ends of the wire mesh form decreases.

In certain embodiments, the spring assembly comprises a one-way viscoelastic spring assembly. The one-way viscoelastic spring assembly may comprise a piston component having first and second nozzles in a head portion of the piston component. The first nozzle can a check valve configured to allow fluid therethrough when a spring of the one-way viscoelastic spring assembly compresses and at least partially inhibit fluid flow therethrough when the spring expands. In certain embodiments, the spring assembly comprises a tuning screw.

The compliance balloon lumen may advantageously be configured to be vacuum sealed using a delivery catheter. In certain embodiments, the compliance restoration device further comprises a first anchor structure. The first anchor structure may be a wire-form anchor. The compliance restoration device may further comprise a second anchor structure coupled to a second end of the compliance balloon lumen, the first anchor structure being coupled to a first end of the compliance balloon lumen. The compliance restoration device may be at least partially collapsible for delivery to a target blood vessel via a catheter delivery system through a minimally-invasive access port. The compliance restoration device may further comprise a central spine structure disposed at least partially within the chamber support structure and is coupled to first and second ends thereof.

In some implementations, the present disclosure relates to a method for treating a heart valve. The method may comprise introducing a compliance restoration device into a target blood vessel in an at least partially collapsed state using a delivery catheter, expanding an anchor structure of the compliance restoration device to contact an inner wall of the target blood vessel, and expanding outward a chamber support structure to support a balloon portion of the compliance restoration device.

The chamber support structure may comprise a wire mesh form, wherein said expanding outward the chamber support structure comprises decreasing a distance between first and second ends of the wire mesh form. In certain embodiments, decreasing the distance between the first and second ends of the wire mesh form comprises pushing the first end of the wire mesh form towards the second end of the wire mesh form using a spring assembly.

In certain embodiments, the spring assembly is a viscoelastic spring assembly. For example, the viscoelastic spring assembly may comprise a piston component having first and second nozzles in a head portion of the piston component. The first nozzle may comprise a check valve configured to allow fluid therethrough when a spring of the viscoelastic spring assembly compresses and at least partially inhibit fluid flow therethrough when the spring expands.

In certain embodiments, the spring assembly comprises a tuning screw. The method may further comprise tuning the spring assembly using the tuning screw.

In certain embodiments, the method comprises inflating the balloon portion to an expanded volume prior to said expanding the chamber support structure. Inflating the balloon portion may comprise injecting a fluid into the balloon portion. The method may further comprise removing the fluid from the balloon portion to form a vacuum and sealing the balloon portion. In certain embodiments, the method further comprises detaching the compliance restoration device from the delivery catheter and increasing the compliance of the target blood vessel using the compliance restoration device.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIGS. 2A and 2B provide cross-sectional and side views, respectively, of a blood vessel experiencing expansion during the systolic phase of the cardiac cycle.

FIGS. 3A and 3B provide cross-sectional and side views, respectively, of the artery shown in FIGS. 2A and 2B during the diastolic phase of the cardiac cycle.

DETAILED DESCRIPTION

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, with respect to any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or apparatuses/devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein. Similar reference numbers may be used with respect to separate diagrams and/or embodiments; use of such similar, or identical, reference numbers should not be interpreted as necessarily identifying identical components, and may refer to separate features.

Overview

In humans and other vertebrate animals, blood circulation throughout the body is facilitated by a blood circulatory system comprising various arteries, capillaries, veins, and coronary vessels, which work together with the heart to supply blood to the various regions of the body. The heart generally comprises a muscular organ having four pumping chambers, wherein the flow thereof is at least partially controlled by various heart valves, namely the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.). The valves may permit fluid flow between the heart and the various arteries of the cardiovascular system.

Figure 1:
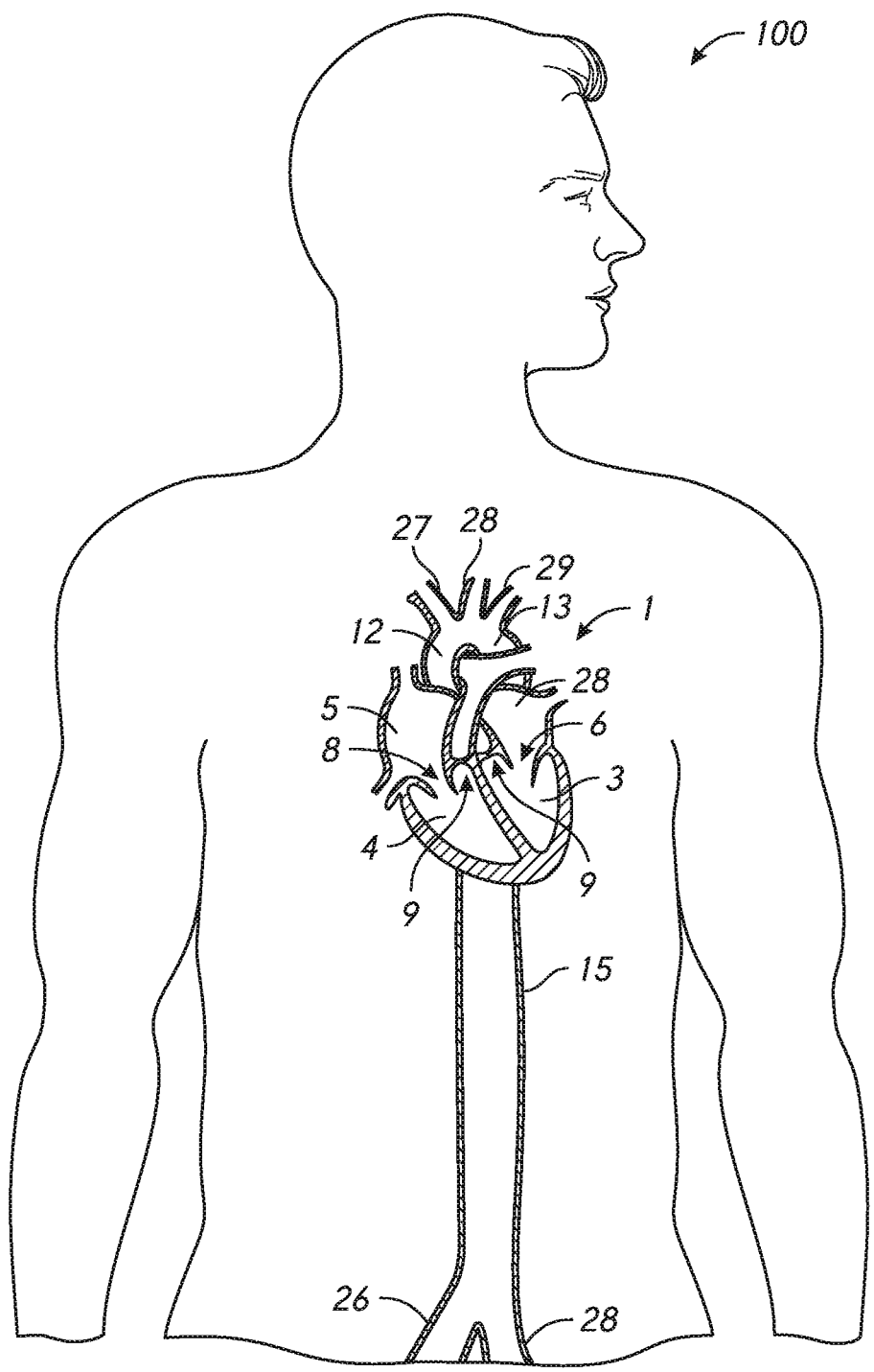
FIG. 1 illustrates an example representation of a heart and associated artery having various features relevant to certain embodiments of the present inventive disclosure.

FIG. 1 illustrates an example representation of a heart 1 and associated artery 15 having various features relevant to certain embodiments of the present inventive disclosure. The heart 1 includes four chambers, namely the left atrium 2, the left ventricle 3, the right ventricle 4, and the right atrium 5. The heart 1 further includes four valves for aiding the circulation of blood therein, including the tricuspid valve 8, which separates the right atrium 5 from the right ventricle 4. The tricuspid valve 8 may generally have three cusps or leaflets and may generally close during ventricular contraction (i.e., systole) and open during ventricular expansion (i.e., diastole). The valves of the heart 1 further include the pulmonary valve 9, which separates the right ventricle 4 from the pulmonary artery 11, and may be configured to open during systole so that blood may be pumped toward the lungs, and close during diastole to prevent blood from leaking back into the heart from the pulmonary artery. The pulmonary valve 9 generally has three cusps/leaflets (not shown). The heart 1 further includes the mitral valve 6, which generally has two cusps/leaflets (not shown) and separates the left atrium 2 from the left ventricle 3. The mitral valve 6 may generally be configured to open during diastole so that blood in the left atrium 2 can flow into the left ventricle 3, and advantageously close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

The aorta is coupled to the heart via the aortic valve 7, wherein the ascending aorta 12 arises from the heart 1 and gives rise to the innominate artery 27, the left common carotid artery 28, and the left subclavian artery 29 before continuing as the descending thoracic aorta 13 and further the abdominal aorta 15.

Arteries, such as the aorta 15, may utilize arterial compliance to store and release energy through the stretching of blood vessel walls. As described herein, arterial "compliance" may refer to the ability of an arterial blood vessel to distend and increase in volume with increasing transmural pressure, or the tendency of an artery, or portion thereof, to resist recoil toward its original dimensions on application of a distending or compressing force. FIGS. 2A and 2B provide cross-sectional and side views, respectively, of a blood vessel 215, such as an artery (e.g., aorta), experiencing expansion during the systolic phase of the cardiac cycle. As understood by those having ordinary skill in the art, the two phases of cardiac cycle are systole and diastole, wherein systole refers to the pumping phase of the left ventricle, while diastole refers to the resting or filling phase. As shown in FIGS. 2A and 2B, with proper arterial compliance, an increase in volume can occur in an artery when the pressure in the artery is increased. With respect to the aorta, as shown in FIGS. 2A and 2B, as blood is pumped into the aorta 215 through the aortic valve 207, the pressure in the aorta increases and the diameter of at least a portion of the aorta expands. A first portion of the blood entering the aorta 215 during systole may pass through the aorta during the systolic phase, while a second portion (e.g., approximately half) may be stored in the expanded aorta provided by arterial compliance, thereby storing energy for contributing to perfusion during the diastolic phase. A compliant aorta may generally stretch with each heartbeat, such that the diameter of at least a portion of the aorta expands.

The tendency of the arteries to stretch in response to pressure as a result of arterial compliance may have a significant effect on perfusion and/or blood pressure in some patients. For example, arteries with relatively higher compliance may be conditioned to more easily deform than lower-compliance arteries under the same pressure and/or volume conditions. Compliance (C) may be calculated using the following equation, where ΔV is the change in volume (e.g., in mL), and ΔP is the pulse pressure from systole to diastole (e.g., in mmHg):

$$C = \frac{\Delta V}{\Delta P} \quad (1)$$

Arterial compliance restoration devices, methods, and concepts disclosed herein may be generally described in the context of the thoracic and/or abdominal aorta. However, it should be understood that such devices, methods and/or concepts may be applicable in connection with any other artery or blood vessel.

FIGS. 3A and 3B provide cross-sectional and side views, respectively, of the artery 215 shown in FIGS. 2A and 2B during the diastolic phase of the cardiac cycle. As shown, arterial compliance may cause retraction of the blood vessel wall inward during diastole, thereby creating pressure to continue to push blood through the artery 215 when the valve 207 is closed. For example, during systole, approximately 50% of the blood that enters the artery 215 through the valve 207 may be passed through the artery, whereas the remaining 50% may be stored in the artery, as enabled by expansion of the vessel wall. Some or all of the stored approximately 50% of blood in the artery 215 may be pushed through the artery by the contracting vessel wall during diastole. For patients experiencing arterial stiffness (i.e., lack of compliance), their arteries may not operate effectively in accordance with the expansion/contraction functionality shown in FIGS. 2A and 2B and FIGS. 3A and 3B.

Figure 4:
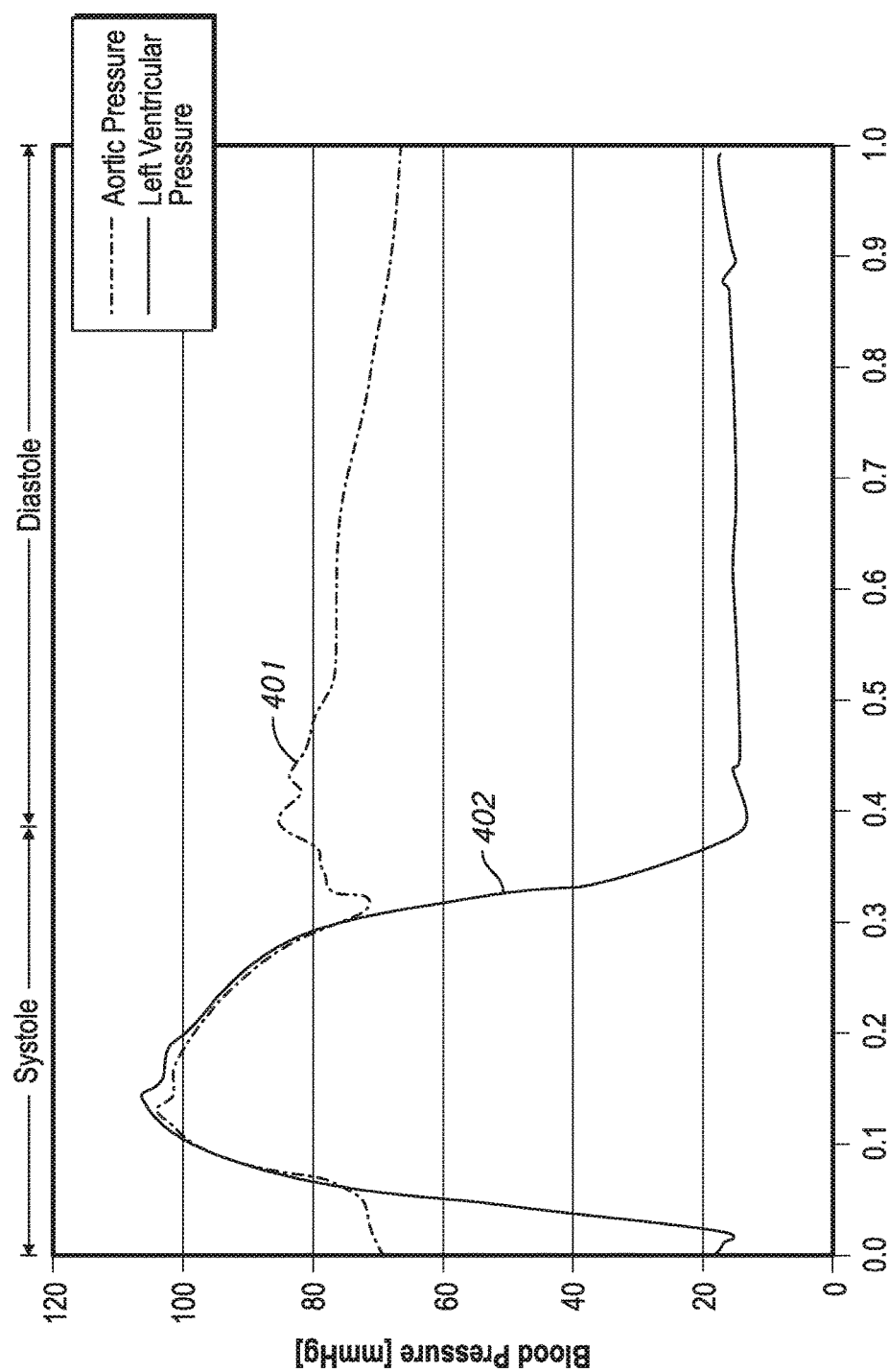
FIG. 4 is a graph illustrating example pressure waves associated with the left ventricle and the aorta of a healthy human patient during a cardiac cycle.

FIG. 4 is a graph illustrating example pressure waves associated with the left ventricle and the aorta of a healthy human patient during a cardiac cycle. During systole, the pressures in the left ventricle and the aorta may be substantially similar, as shown. After systole, the pressure in the left ventricle may advantageously drop to create a sufficient pressure gradient between the aorta and the left ventricle in order to allow for blood to overcome vascular resistance and provide sufficient perfusion of the heart muscle. Aortic compliance, as described above, can serve to maintain the desired gradient for at least a portion of the diastolic phase.

Reduced arterial compliance may generally be caused by one or more of a variety of factors. For example, endothelial dysfunction, which may be associated with hypertension in patients, may result in reduced compliance, particularly in the smaller arteries. Reduced arterial compliance may also present in patients with diabetes, and also in smokers, and arterial compliance may also diminish with age, and in connection with menopause. Reduced arterial compliance may further elevate blood pressure, thereby further causing atherosclerosis (i.e., hardening of the arteries), and leading to increased cardiovascular risk. Arterial compliance can be measured by various techniques, such as pulse contour analysis or other non-invasive methods.

Patients with reduced arterial compliance may experience reduced perfusion, including cardiac perfusion, which may result in various health complications in human patients, including organ and/or tissue failure due to insufficient perfusion. Furthermore, low compliance may result in increased strain of the heart muscle, as well as reduction in coronary perfusion. Failure to properly treat reduced compliance in certain patients can result in serious injury and/or death under certain conditions.

Figure 5:
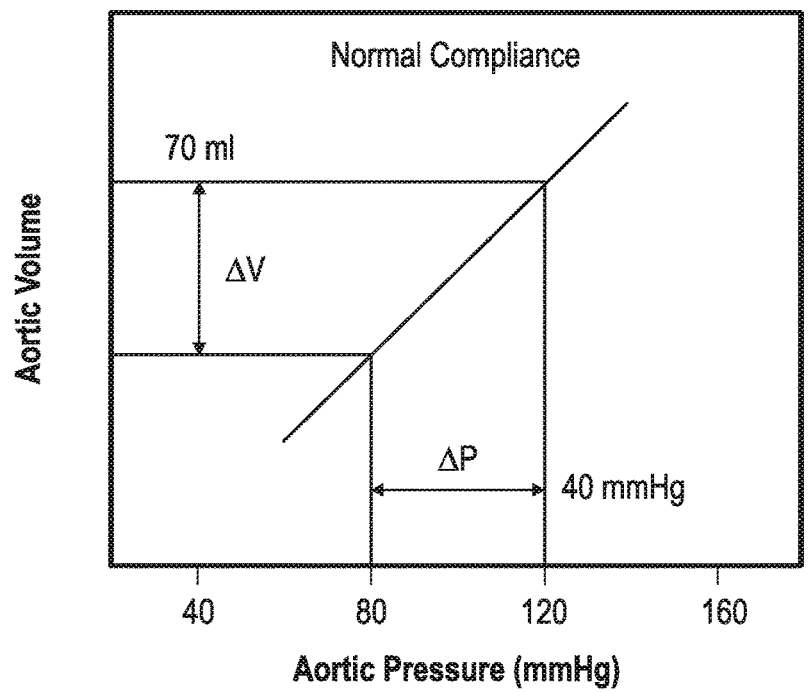
FIG. 5 is a graph illustrating aortic volume relative to pulse pressure for an example aorta having normal compliance characteristics.

FIG. 5 is a graph illustrating aortic volume relative to pulse pressure for an example aorta having normal compliance characteristics. Assuming constant stroke volume, pulse pressure may represent a primary variable in assessing aortic compliance. For a patient having normal arterial compliance, such compliance may have a value of about 1.5 in view of equation (1), presented above. For example, compliance in a healthy patient may be based on a change in aortic volume of approximately 70 mL being associated with a change in pressure of approximately 40 mmHG.

Figure 6:
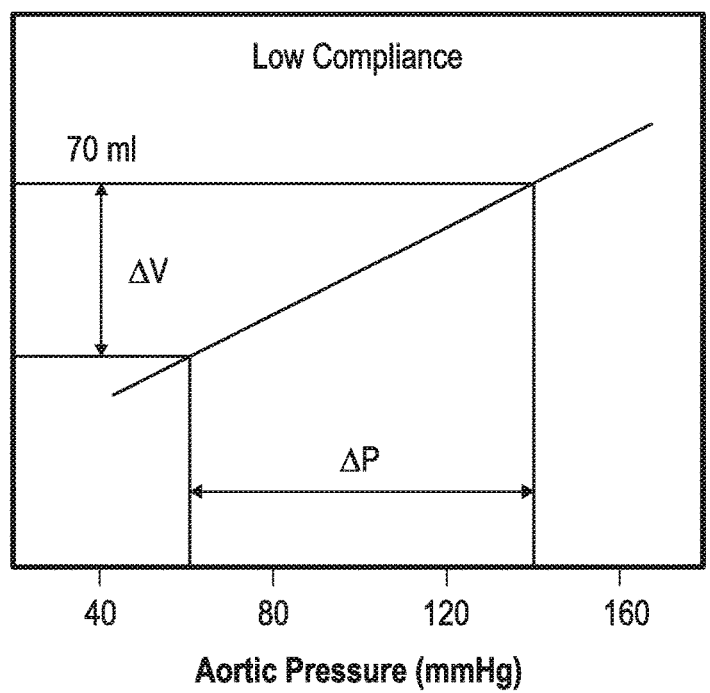
FIG. 6 is a graph illustrating aortic volume relative to pulse pressure for an example aorta having low compliance characteristics.

FIG. 6 is a graph illustrating aortic volume relative to pulse pressure for an example aorta having low compliance characteristics. The graph of FIG. 6 represents the effect compliance reduction may have on the aortic pressure waveform. For a patient having low arterial compliance, such compliance may have a value of about 0.9 in view of equation (1), presented above. For example, compliance in a patient with arterial stiffness may be based on a change in aortic volume of approximately 70 ml being associated with a change in pressure of approximately 80 mmHG. As noted above, arterial compliance may tend to decrease with age.

Figure 7:
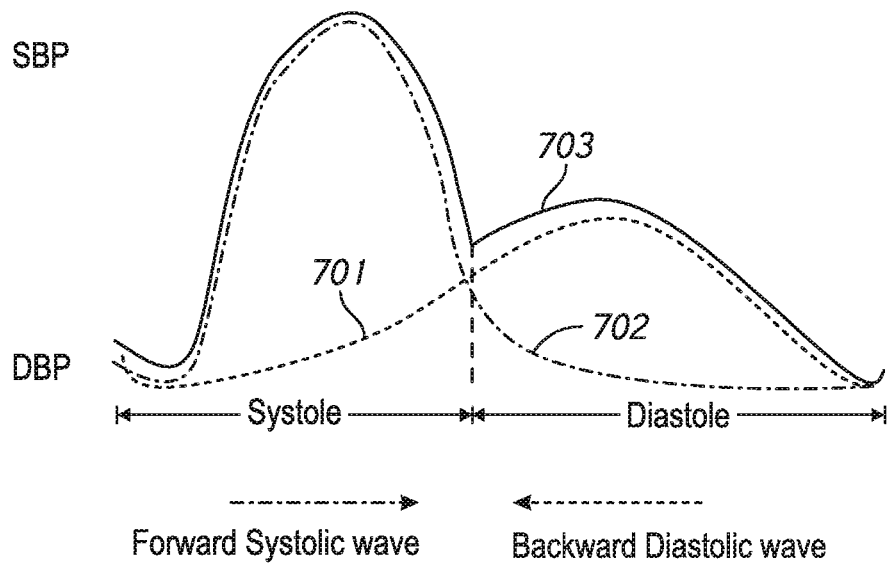
FIG. 7 is a graph illustrating blood pressure over time in an example healthy patient.

FIG. 7 is a graph illustrating blood pressure over time in an example healthy patient, wherein arterial blood pressure is represented as a combination of a forward systolic pressure wave 701 and a backward diastolic pressure wave 702. The combination of the systolic wave 701 and the diastolic wave 702 are represented by the waveform 703.

Figure 8:
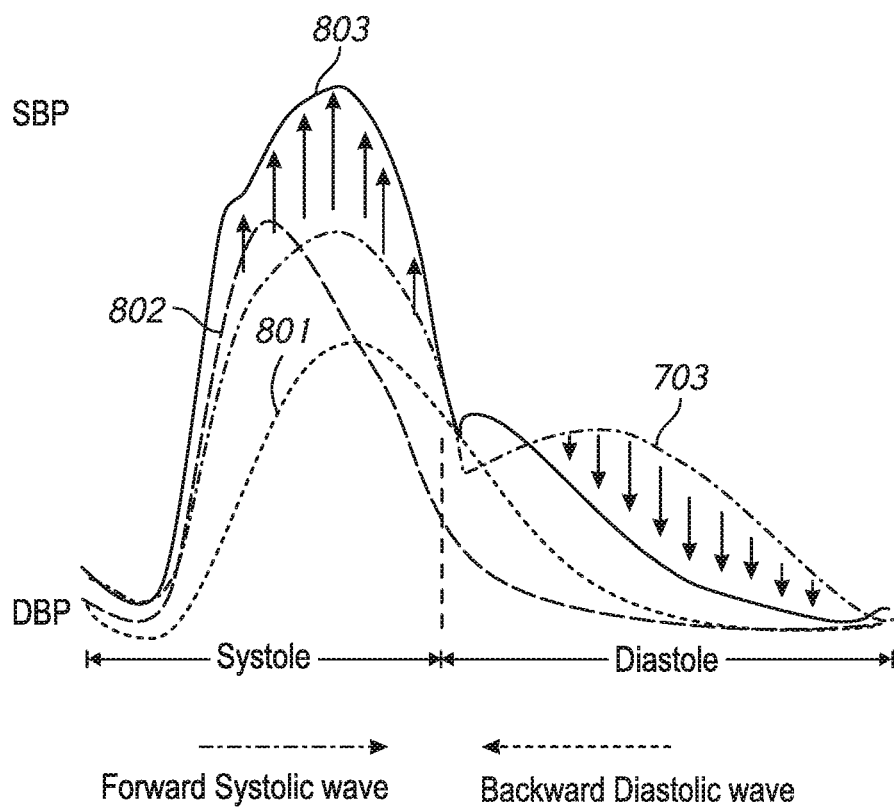
FIG. 8 is a graph illustrating blood pressure over time in an example patient having reduced aortic compliance.

FIG. 8 is a graph illustrating blood pressure over time in an example patient having reduced aortic compliance. The graph of FIG. 8 shows, for reference purposes, the example combined wave 703 shown in FIG. 7. When low compliance is exhibited, less energy may be stored in the aorta compared to a healthy patient. Therefore, the systolic waveform 802 may demonstrate increased pressure relative to a patient having normal compliance, while the diastolic waveform 801 may demonstrate reduced pressure relative to a patient having normal compliance. Therefore, the resulting combined waveform 803 may represent an increase in the systolic peak and a drop in the diastolic pressure, which may cause various health complications. For example, the change in waveform may impact the work load on the left ventricle, and may adversely affect coronary profusion.

In view of the health complications that may be associated with reduces arterial compliance, as described above, it may be desirable in certain patients and/or under certain conditions, to at least partially alter compliance properties of the aorta or other artery or blood vessel in order to improve cardiac and/or other organ health. Disclosed herein are various devices and methods for at least partially restoring compliance to a blood vessel, such as the aorta. Certain embodiments disclosed herein achieve restoration of arterial compliance through the use of implantable vacuum-based compliance balloon devices. For example, a compliance restoration device in accordance with the present disclosure may comprise a collapsible hollow chamber, such as a balloon, that is inserted in a collapsed state by a catheter and further deployed and anchored in an artery (e.g., aorta) or other blood vessel. The device may be anchored to the blood vessel wall using a wire-form or stent anchor, as described in greater detail herein. Although certain embodiments of compliance restoration devices are described herein in the context of deployment in the aorta, it should be understood that compliance restoration devices in accordance with the present disclosure may be deployed in any chamber of the heart or any major artery or vein that may benefit from increased compliance characteristics. Compliance restoration devices disclosed herein may serve to at least partially increase coronary perfusion.

Compliance Restoration Devices and Methods

Arterial compliance can serve to promote adequate perfusion of organs in the body. As described above, the aorta and other major arteries in the body are advantageously at least partially elastic and compliant, and therefore can act as reservoirs of blood, filling with blood when the heart contracts during systole and continuing to generate pressure and push blood to body organs during diastole. In older patients, patients suffering from heart failure and atherosclerosis, and/or other types of patients, compliance of the aorta and arteries can be diminished or lost, thereby reducing the supply of blood to body organs due to the reduction of blood flow during diastole. A substantial risk associated with reduction in diastolic flow is the risk of insufficient blood supply to the heart muscle itself. During systole, flow of blood in the coronary arteries and into the heart muscle can be substantially reduced due to the heart being contracted and held at high pressure. During diastole, the heart muscle relaxes and allows flow. Perfusion of the heart muscle may generally rely on diastolic flow, and therefor on aortic compliance. In chronic heart failure patients, cardiac output may be inadequate in supplying the body demand for perfusion. Loss of aortic compliance can create a bias for under-perfusion of the heart muscle. Disclosed herein are devices and methods for restoring compliance to the aorta (or other blood vessel) and creating a counter bias for improved perfusion of the heart muscle. Utilization of devices and/or methods disclosed herein may advantageously impede the progression of chronic heart failure and/or reduce or reverse its symptoms.

Figure 9:
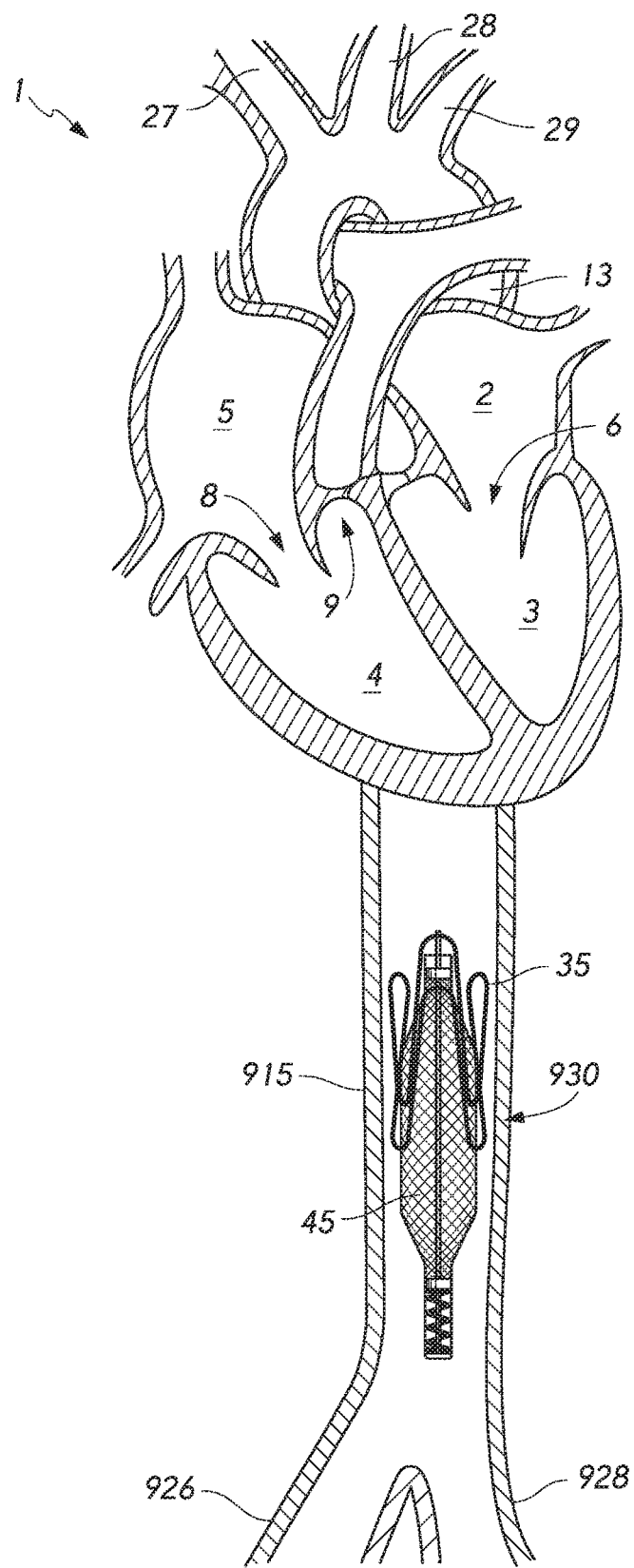
FIG. 9 illustrates a compliance restoration device implemented in an aorta according to one or more embodiments.

FIG. 9 illustrates a compliance restoration device 930 implemented in an aorta according to one or more embodiments. Although the device 930 is shown as implemented in the aorta, it should be understood that compliance restoration devices in accordance with the present disclosure may be implemented in any suitable or desirable blood vessel in order to improve compliance characteristics associated therewith. For patients in which aortic compliance is at least partially compromised, an implant in the aorta, such as an implant similar to the device 930, may serve to add compliance back to the aortic system. For example, in certain embodiments, the compliance restoration device 930 comprises a substitute compliance lumen, or chamber 45. that is configured to store and release energy in a manner similar to the functioning of a healthy, compliant aorta. As shown in FIG. 9, the compliance restoration device 930 may be implanted in the abdominal aorta 915 of a patient. Access to the abdominal aorta 915 may be achieved, for example, through one of the right 926 or left 928 femoral arteries, or through another access point.

In certain embodiments, the implanted lumen/chamber 45 is configured to be fully expanded at external pressure of around 80 mmHg, or less, and collapse to a lower volume at pressures higher than 80 mmHg. The compliance chamber 45 may advantageously lose as much volume as possible when reaching around 120 mmHg, for example. As used herein, references to blood pressure values in units of millimeters of mercury (mmHg) may refer to pressure relative to the surrounding atmospheric pressure, which is 760 mmHg at sea level. Therefore, a described change from 120 mmHg to 80 mmHg may represent an actual change from 880 mmHg (i.e., 760 mmHg+120 mmHg) to 840 mmHg (i.e., 760 mmHg+80 mmHg) at sea level, which represents a change of less than 5% in absolute pressure. In embodiments comprising a gas- or fluid-filled balloon as a compliance chamber, the balloon may experience relatively little or no variation in volume at normal atmospheric due to the relatively low compressibility of gasses at body temperature, and non-compressibility of fluids; a change in absolute pressure of less than 5% between 120 mmHg and 80 mmHg may result in compression of a gas-filled balloon by less than 5% of its volume. Therefore, a relatively large balloon may be necessary in order to achieve a significant change in compliance using a gas-filled balloon.

In certain embodiments, the compliance chamber 45 of the compliance restoration device 930 is free, or emptied, of gas and/or fluid, such as through the application of a vacuum thereto. The compliance chamber 45 may remain in an expanded state using one or more internal mechanical supports. For example, such support(s) may comprise one or more elastic wires and/or springs; wire and spring assemblies are described in greater detail below. The mechanical structure of the compliance restoration device 930, compliance chamber 45 and/or chamber support(s) may provide the desired physiological compliance.

Certain embodiments of compliance restoration devices in accordance with the present disclosure comprise a collapsible, hollow chamber, such as a balloon-type chamber, that may be inserted into the target blood vessel in an at least partially collapsed state using a catheter delivery system. Compliance restoration devices may further be deployed and/or anchored in the target blood vessel (e.g., aorta) using, for example, a wire-form anchor 35 or other stent structure, as shown in FIG. 9. Although the compliance restoration device 930 is shown deployed in the abdominal aorta 915, it should be understood that compliance restoration devices in accordance with embodiments of the present disclosure may be deployed at any position or location in the aorta. Furthermore, although a single compliance restoration device is shown, in certain embodiments, multiple compliance restoration devices as described herein may be deployed in the aorta and/or other blood vessel(s) in order to achieve the desired vascular compliance.

The compliance restoration device 930 may be implanted using a delivery lumen (not shown) through which the device 930 may be passed to the target location within the aorta. In certain embodiments, real-time visualization tools may be used to evaluate the implant position and/or functionality of the device 930, such as ultrasound, nuclear magnetic resonance, or other visualization technology. The operator may place and/or configure the compliance restoration device 930 in the target location at least in part by manipulating one or more distal control leads associated with the catheter delivery system. The device 930 may advantageously be placed and/or configured to avoid undesired obstruction of blood flow through the aorta.

Figure 10:
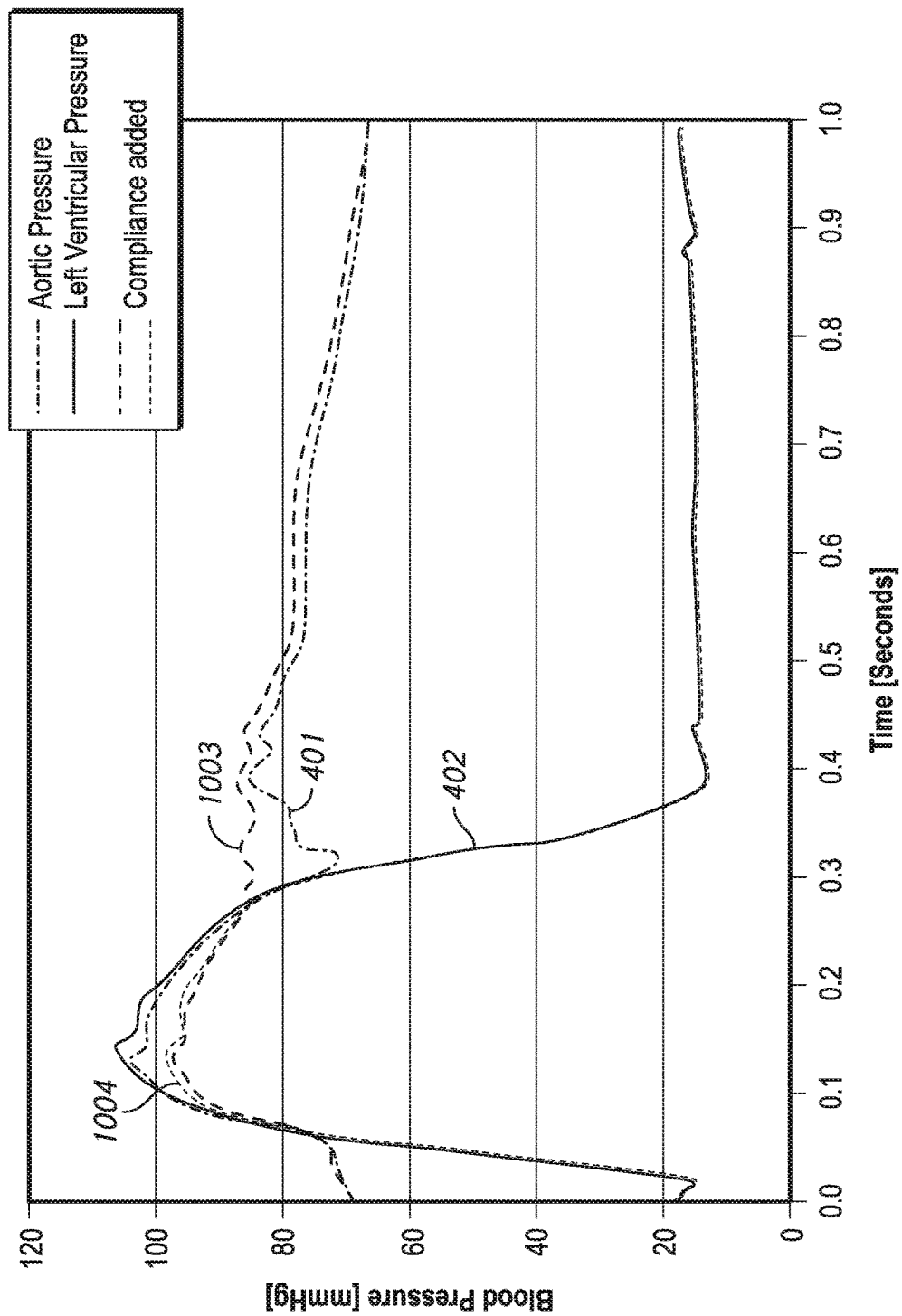
FIG. 10 is a graph illustrating example pressure waves associated with the left ventricle and the aorta of an example patient having a compliance restoration device in accordance with one or more embodiments.

FIG. 10 is a graph illustrating example pressure waves associated with the left ventricle and the aorta of an example patient having a compliance restoration device in accordance with one or more embodiments disclosed herein implanted in the aorta. As shown in FIG. 10, in certain embodiments, the resulting changes in blood pressure as a result of implantation of a compliance restoration device may include smoothing-out of the pressure wave. Compliance restoration in accordance with the present disclosure may cause an at least partial reduction in the systolic pressure, thereby making it easier for the left ventricle to pump blood into the more compliant aortic cavity as the compliance chamber of the compliance restoration device collapses. Implantation of a compliance restoration device may also at least partially increase the diastolic pressure in the aorta and/or push increased blood volume over extended periods of time to body organs, as well as possibly to the heart muscle, as the compliance chamber recovers its expanded volume.

As described above, compliance restoration in certain patients may serve to at least partially reduce the stress that the left ventricle may be subjected to in connection with reduced arterial compliance. By reducing the stress on the left ventricle, longevity of the heart may be improved in certain patients. In addition, restoration of lost arterial compliance may at least partially improve coronary profusion by increasing the amount of blood that is supplied to the heart muscles from the aorta, for example.

Figure 11:
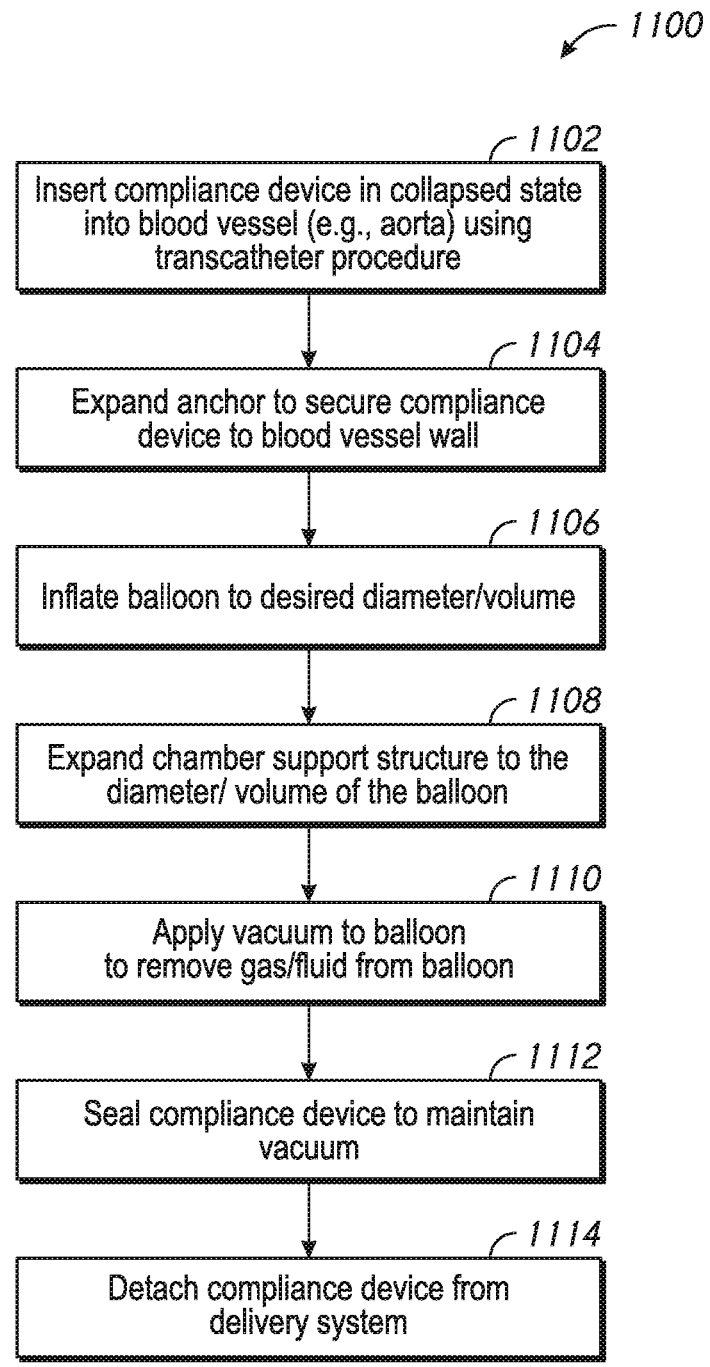
FIG. 11 is a flow diagram of a process for restoring compliance to a blood vessel in accordance with one or more embodiments.

FIG. 11 is a flow diagram of a process 1100 for restoring compliance to a blood vessel in accordance with one or more embodiments. At block 1102, the process 1100 involves inserting a compliance restoration device in accordance with one or more embodiments disclosed herein into a target blood vessel using a transcatheter procedure. Although transcatheter implantation is disclosed herein in the context of certain embodiments, it should be understood that any type of implantation may be implemented in connection with compliance restoration devices disclosed herein. The target blood vessel may be an artery, such as the aorta. The target location within the target blood vessel may be any suitable or desirable location within the respective blood vessel. The various steps of the process 1100 of FIG. 11 may be understood with reference to certain of the diagrams presented in FIGS. 12A-12E and described in detail below.

Figure 12A:
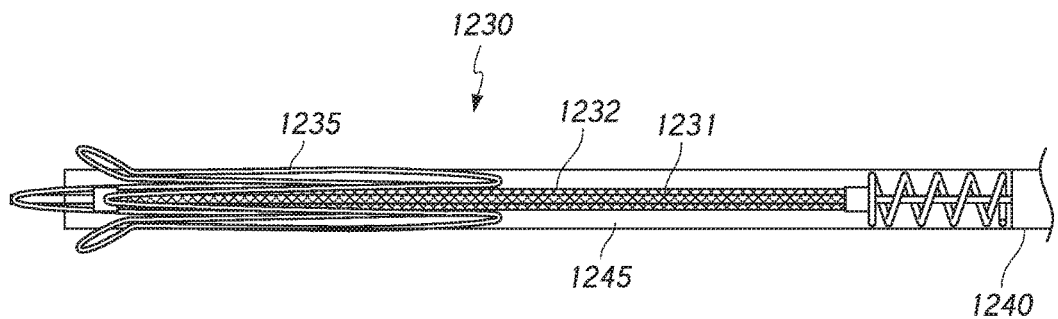
FIGS. 12A-12E provide diagrams of a compliance restoration device 1230 in various stages of deployment according to one or more embodiments.

The compliance restoration device may be inserted in an at least partially collapsed state, as shown in FIG. 12A, which provides a side view of a compliance restoration device 1230 in accordance with one or more embodiments of the present disclosure. The collapsed compliance restoration device 1230 may include a central spine 1231 for mounting and/or securing one or more components of the compliance restoration device 1320. The spine 1231 may comprise a lumen to facilitate deployment over a guide wire. The spine 1231 may further comprise a mechanism for attaching and/or detaching the compliance restoration device 1230 from a delivery catheter 1240. In certain embodiments, the compliance restoration device 1230 does not comprise the central spine 1231.

The compliance restoration device 1230 may further include a chamber support structure 1232, such as a braded wire mesh or other wire support form, which may be mounted or secured to at least a portion of the spine component 1231. In FIG. 12A, the chamber support structure 1232 is shown in a collapsed state, which may allow for delivery of the compliance restoration device 1230 at least partially within the catheter delivery system.

The compliance restoration device 1230 may further include a balloon lumen 1245 mounted over the chamber support structure 1232 (e.g., braided mesh system), wherein the balloon 1245 is configured to be expanded to thereby form a compliance chamber therein. The chamber support structure 1232 may serve as a mechanical support for the balloon 1245, wherein the chamber support structure 1232 may be at least partially surrounded by the balloon 1245 such that the chamber support structure 1235 is configured to exert outward force on an inner surface of the balloon 1245 to prevent or reduce collapsing by the balloon 1245. The balloon lumen 1245 may be sealed to form an internal volume that provides the compliance chamber. In certain embodiments, the balloon 1245 may be able to hold a vacuum therein to provide a vacuum chamber, as described in greater detail below.

The compliance restoration device 1230 may further include an anchor structure 1235, which may serve to at least partially secure the compliance restoration device 1230 in a target position within the target blood vessel. FIG. 12A shows the anchor structure 1235 in an at least partially collapsed state to facilitate passage in the target blood vessel using the catheter delivery system. The anchor structure 1235 may be a wire-form, as shown, or may have any other desirable or suitable form. As shown in FIG. 12A, some or all of the various components of the compliance restoration device 930 may be at least partially collapsible and/or compressible to allow for minimally invasive insertion and/or implantation using the catheter 1240. While the compliance restoration device 1230 is described in connection with certain figures and/or embodiments as being implanted in the aorta, the device 1230 can be configured to be deployed in any chamber of the heart or any major artery or vein that requires additional compliance.

Figure 12B:
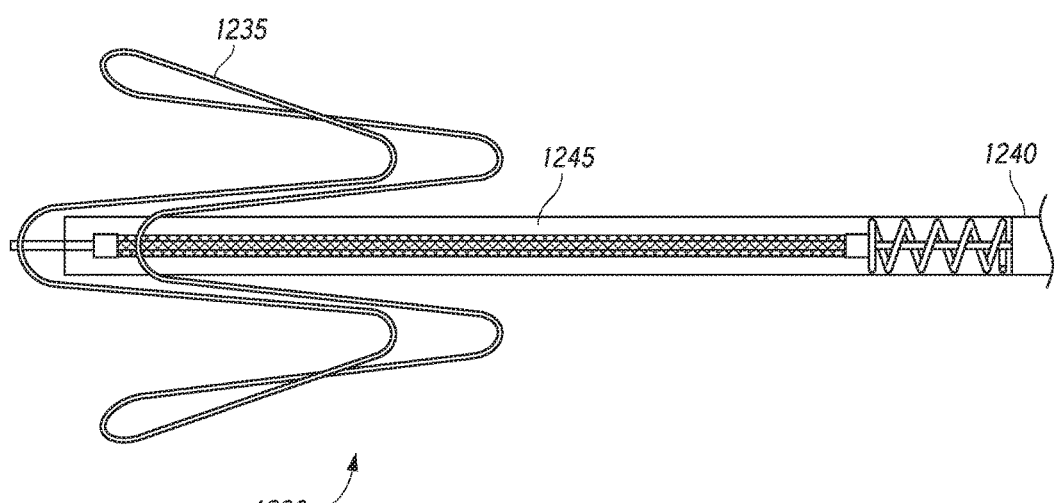

FIGS. 12B-12E provide additional diagrams of the compliance restoration device 1230 in various stages of deployment to further illustrate the function and/or features of the various components/features thereof, which may be understood with reference to the flow diagram of FIG. 11. With further reference to FIG. 11, the process 1100 may involve, at block 1104, expanding the anchor 1235 in order to secure the compliance restoration device 1230 to the wall of the target blood vessel, as shown in FIG. 12B. For example, where the device 1230 is implanted in the aorta, which may have a diameter of approximately 3-4 cm, the anchor structure 1235 may be configured to expand to a diameter of the target blood vessel in order to achieve a tension contact therewith.

FIG. 12B shows the anchor structure 1235 in a deployed state. In certain embodiments, the anchor 1235 may comprise a self-expanding memory metal (e.g., Nitinol) structure that engages the blood vessel wall. The anchor 1235 may advantageously be expanded to apply outward radial force against the inner wall of the target blood vessel, thereby creating tension force to hold the compliance restoration device 1230 in place. In certain embodiments, the anchor 1235 may be configured to put out more than 200 mmHg pressure, such as 250 mmHg or more. The anchor structure 1235 may effectively operate as a stent structure, although the anchor 1235 may not be designed to hold the target blood vessel open, but rather to secure the compliance restoration device 930 in place within the blood vessel.

The anchor structure 1235 may advantageously be at least partially flexible to account for blood vessel compliance. In certain embodiments, the anchor 1235 may be tunable depending on the amount of drag generally present around the balloon. Once deployed, the anchor structure 1235 may ultimately become at least partially in-grown into the blood vessel wall. The material of which the anchor is comprised, and/or a coating or other material associated with the anchor 1235, may have characteristics that impede tissue overgrowth, which may advantageously protect against blood flow obstruction.

Figure 12C:
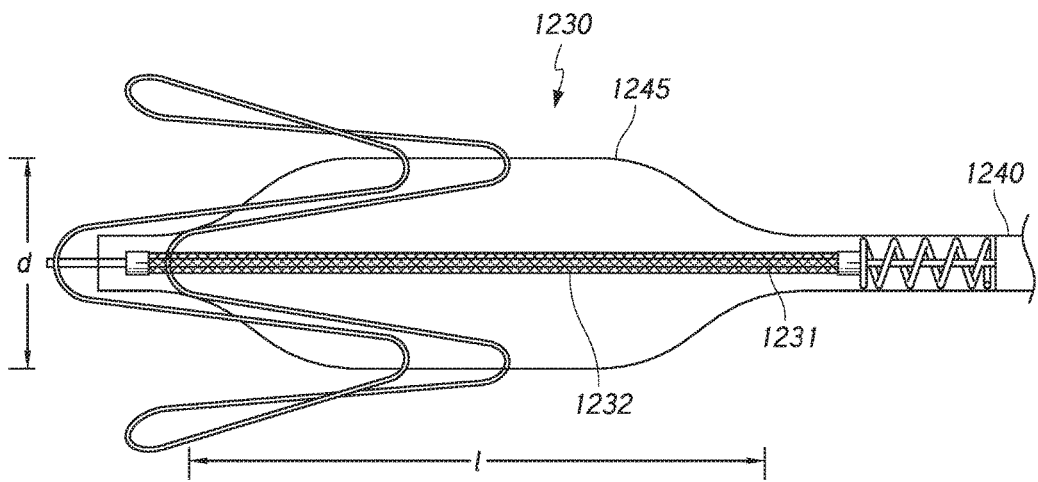

With further reference to FIG. 11, at block 1106, the process 1100 may involve inflating the balloon lumen 1245 to a desired diameter $d_1$ and/or volume, as shown in FIG. 12C. For example, the balloon 1245 may be inflated with fluid or gas, such as through the use of a balloon inflation lumen. The balloon 1245 may have any suitable or desirable expanded shape.

The balloon 1245 may advantageously be designed to have a length $l_1$ and/or diameter $d_1$ sufficient to provide the desired volume, while maintaining a diameter small enough to avoid obstruction of blood flow. For example, the balloon 1245 may have a length $l_1$ of approximately 15 cm, or less. In certain embodiments, the balloon 1245 may have a length $l_1$ of between 15-20 cm. In certain embodiments, the balloon 1245 may have a length $l_1$ of approximately 20 cm, or greater. In certain embodiments, the balloon 1245 may be configured to have a compressed diameter of approximately 0.4 cm, or some other value. The balloon 1245 may have an expanded diameter $d_1$ of approximately 1.2 cm, or less. In certain embodiments, the balloon 1245 may have an expanded diameter $d_1$ of between approximately 1.2-2.0 cm. In certain embodiments, the balloon 1245 may have an expanded diameter $d_1$ of approximately 2.0 cm, or greater. With longer balloons, it may be suitable to utilize an expanded diameter that is relatively less in order to provide the same effective working volume.

In certain embodiments, the balloon may comprise a polymer material having characteristics that provide for fluid and/or gas barrier sealing. In accordance with step 1106, the balloon may be inflated with a gas that at least partially dissolves in blood, such as $CO_2$. In certain embodiments, the process 1100 may not involve inflating the balloon 1245 with fluid or gas. That is, in certain embodiments, the process 1100 may not include the step 1106.

Figure 12D:
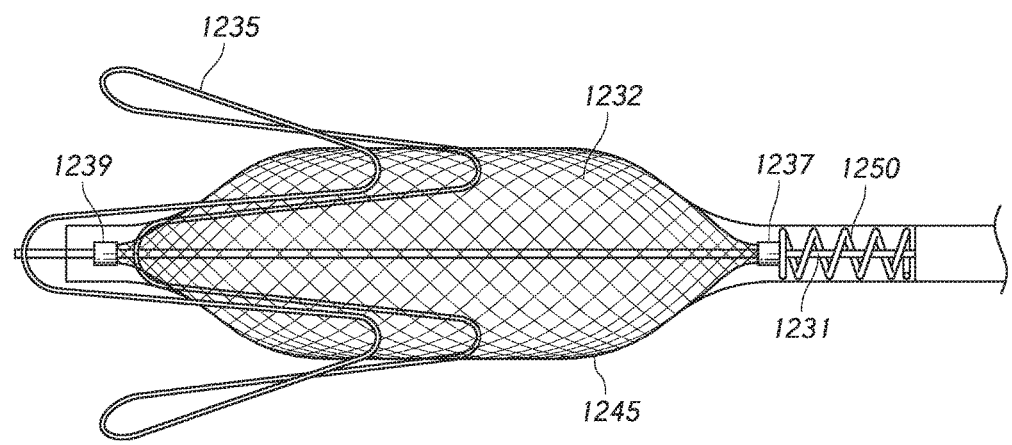

With further reference to FIG. 11, at block 1108, the process 1100 may involve expanding the chamber support structure 1232 (e.g., wire mesh) to the diameter and/or volume of the inflated balloon in order to provide support for the balloon in the expanded state, as shown in FIG. 12D. The chamber support structure 1235 may be configured to expand to fill, or at least partially fill, the volume of the chamber created by the inflated balloon 1245. In some embodiments, the chamber support structure 1232 (e.g., wire mesh) may be expanded inside a collapsed balloon; that is, the balloon may not have been inflated to a desired diameter or volume prior to expanding the chamber support structure.

Expansion of the chamber support structure 1232 may be achieved at least in part through the shortening of the chamber support structure 1232 from end-to-end, wherein the chamber support structure 1232 may be configured such that drawing the ends 1239, 1237 towards each other along a central axis of the compliance restoration device 1230 may cause an inner portion of the structure to expand outward, as shown. One or more of the ends 1239, 1237 of the chamber support structure 1232 may be secured to the central spine component 1231. In certain embodiments, the longitudinal shortening of the chamber support structure may be achieved through pushing on the end 1237 of the chamber support structure 1232 in a direction towards the distal end 1239 of the chamber support structure.

The chamber support structure 1235 may operate in connection with one or more springs 1250, which may provide spring-loading tension on the chamber support structure 1232 in order to provide flexibility in the expansion of the chamber support structure 1232. The spring 1250 may be in direct physical contact with at least a portion of the end 1237 of the chamber support structure 1232. For example, the spring 1250 may be secured to, or otherwise contact, the end portion 1237 of the chamber support structure 1232. In certain embodiments, the spring 1250 may be compressed to approximately 10-15% of its non-compressed length when deployed, such that relatively small changes in length of the spring 1250 may have a relatively large effect on the pressure applied to the chamber support structure 1232 by the spring 1250. The spring 1250 may advantageously be sufficiently long to avoid fatigue on the wire/metal element of the spring; that is, the spring 1250 may be dimensioned such that it operates within the fatigue limit of the spring during deployed operation in the target blood vessel.

FIG. 12D illustrates the chamber support structure 1232, which is illustrated as a braided wire mesh structure, in a shortened and expanded state, wherein the expansion of the support structure 1232 is associated with the diameter of the balloon 1245 in order to provide support to the balloon 1245 from within. In certain embodiments, the chamber support structure 1232 is at least partially elastic, wherein the desired compliance of the balloon 1245 and support structure 1232 is maintained by the spring 1250. The proximal end of the spring 1250 may be fixed to the spine 1231 under compressive tension, thereby creating the desired preload for holding up the chamber support structure 1232 (e.g., braided wire mesh).

After deploying the support system comprising the support structure 1232 and the spring 1250, gas and/or fluid may be removed from the balloon 1245, such as by applying a vacuum to the balloon through, for example, the balloon inflation lumen. For example, as shown at block 1110, the process 1100 may involve applying a vacuum to the compliance restoration device to remove some or all of the gas or fluid from the balloon lumen 1245. In certain embodiments, the compliance restoration device 1230 and/or associated delivery system may include a tube configured to pull vacuum and to be detached and withdrawn. Advantageously, the balloon lumen 1245 may not substantially collapse when the gas and/or fluid is extracted because the chamber support structure 1232 holds it in the expanded state. After gas and/or fluid has been successfully removed from the balloon, the inflation lumen may be sealed to hold the vacuum. In certain embodiments, the balloon 1245 comprises material that can hold the vacuum for prolonged periods of time. For example, the balloon may comprise a multi-layered polymer and/or metallic foil.

In order to compensate for varying physiology of different patients, the compliance restoration device 1230 may allow for compliance tuning. For example, the compliance restoration device 1230 and/or catheter 1240 may comprise a thread or other mechanism (see, e.g., FIG. 16 and the associated description below) for determining a degree of compression of the spring 1250. Through the use of, for example, a pressure cuff or other physiological monitor, the operator may determine the desired position/tension of the spring 1250, such that the spring 1250 may be tuned to the patient using the pressure cuff reading, and/or other physiological sensor reading, as feedback. In certain embodiments, tuning may be performed using echocardiography to monitor the effect of the implanted compliance restoration device. Tuning may be performed to achieve maximum and/or desirable cardiac output using the compliance restoration device 1230.

In certain embodiments, it may be desirable for the volume of the compliance balloon lumen 1245 to change between approximately 20-50 mL between systole and diastole. Where the balloon lumen 1245 is configured to collapse by a relatively greater volume, it may be possible to achieve desired compliance using a relatively smaller balloon and/or compliance restoration device. In certain embodiments, it may only be necessary for the balloon 1245 to collapse by 20 mL for patients with relatively better aortic compliance, whereas greater collapsibility may be desired for patients with stiffer aortas. In certain embodiments, the balloon 1245 may have a working volume of between 10-50 mL. In certain embodiments, the balloon 1245 has a working volume of approximately 16 ml, which may serve to restore compliance from a value of approximately 0.9 to approximately 1.3.

In certain embodiments, the chamber support structure 1232 comprises a plurality of wires configured to open and close in response to pressure. Although braided wire mesh support structures are illustrated and described in connection with certain embodiments of the present disclosure, it should be understood that any type of support structure may be implemented, wherein the structure, such as wire(s) or the like, is configured to store and release energy in response to changes in ambient pressure.

At block 1112, the process 1100 may involve sealing the compliance restoration device to maintain the vacuum within the balloon lumen 1245. At block 1114, the process 1100 may involve detaching the compliance restoration device 1230 from the delivery system in order to deploy the compliance restoration device within the target blood vessel for on-going, post-operative compliance restoration for the target blood vessel. The delivery system may then be withdrawn from the implantation site.

Figure 12E:
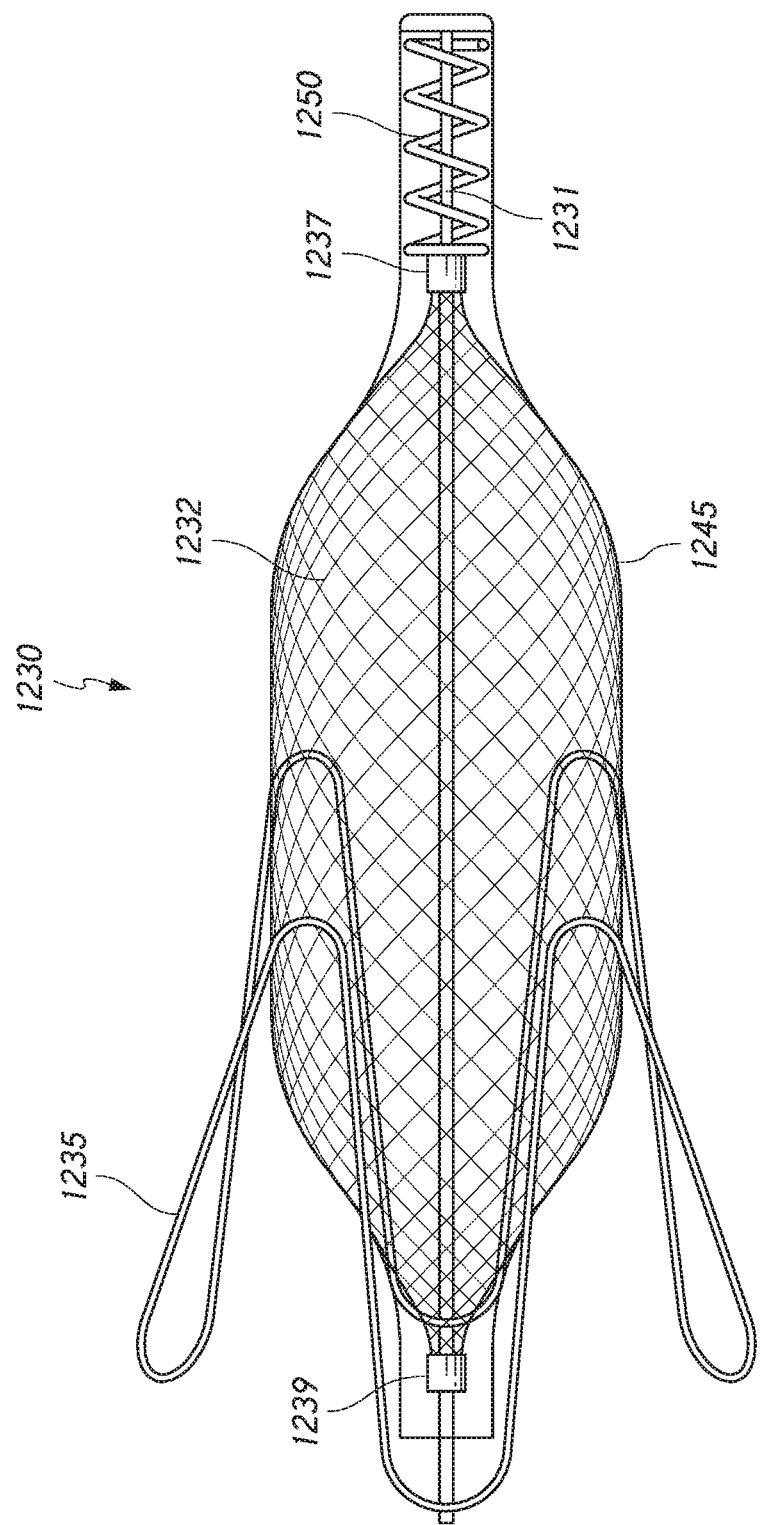

After verifying the desired compliance and desired changes to aortic blood pressure, the delivery catheter 1240 may be detached from the compliance restoration device 1230. FIG. 12E illustrates the compliance restoration device 1230 in its final deployed state, detached from the delivery catheter. In certain embodiments, the deployed compliance restoration device may include an expanded compliance chamber with a spring-containing appendage extending therefrom, as shown. In certain embodiments, the compliance restoration device 1230 may be configured to be removable from the implant site after deployment therein. For example, in some embodiments, the compliance restoration device 1230 may be configured to be detached from the anchor structure 1235 and removed from the implant site independently of the anchor structure 1235. In its deployed state, the compliance restoration device 1230 may operate to provide compliance back to the cardiovascular system, thereby reducing the strain on the heart muscle and improving perfusion to one or more regions of the body and to the heart.

Compliance Balloon Expansion Control

Figure 13A:
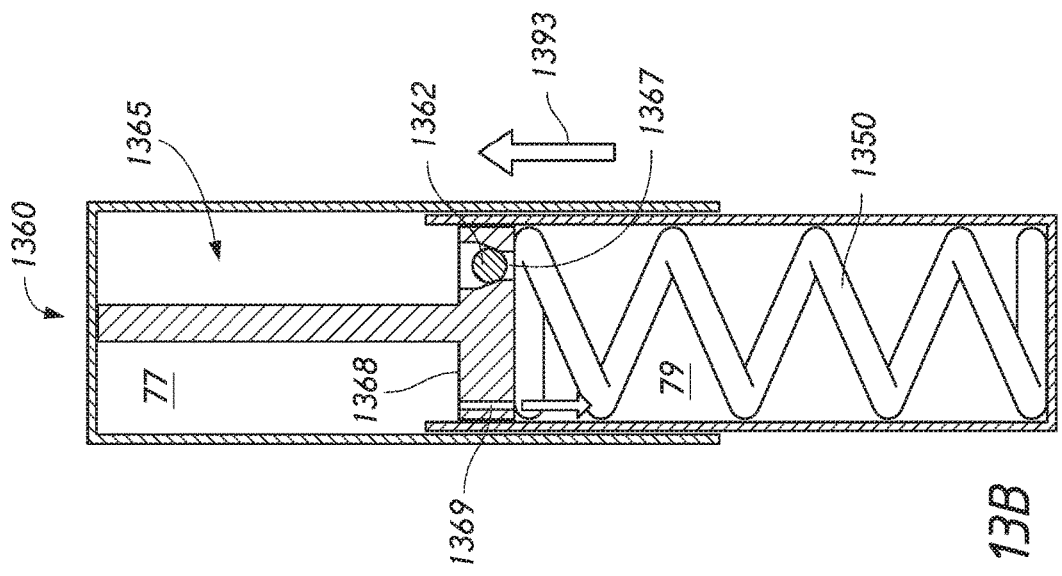
FIGS. 13A and 13B illustrate a viscoelastic spring assembly in accordance with one or more embodiments in compressed and expanded states, respectively.
Figure 13B:
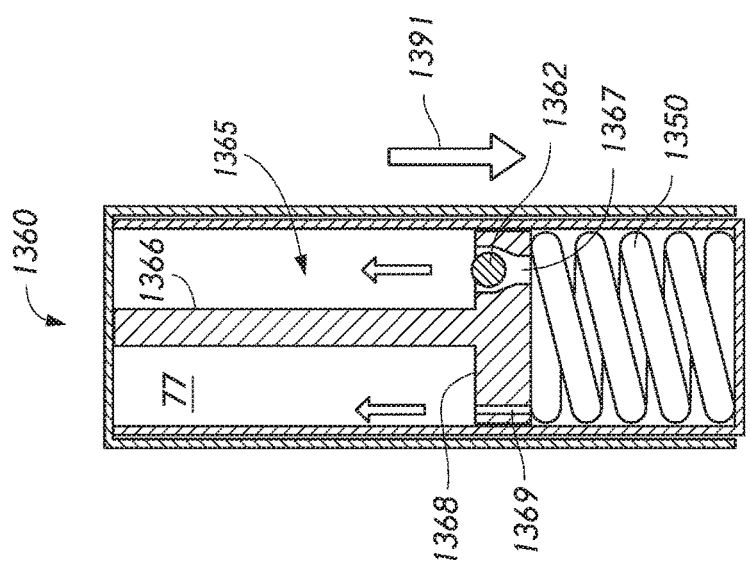

In certain embodiments, it may be desirable to control the rate at which a compliance balloon/chamber of a compliance restoration device in accordance with the present disclosure expands and/or contracts. Controlling the rate of expansion and/or contraction may advantageously help to further smooth out the pressure waveform. For example, in some embodiments, diastolic flow may be improved by providing a compliance balloon that collapses relatively quickly during systole but recovers more slowly when external pressure is lowered during diastole. FIGS. 13A and 13B illustrate a viscoelastic spring assembly 1360 in accordance with one or more embodiments in compressed and expanded states, respectively. The spring assembly 1360 may comprise a piston member 1365 and a spring 1350, wherein the piston member 1365 comprises a head portion 1368 and a rod portion 1366. The piston member 1365 may be disposed in a first chamber 77, which may be at least partially filled with fluid, while the spring may be disposed in a second chamber 79 that may likewise be at least partially filled with fluid. The head portion 1368 may be designed to physical compress the spring 1350 when inward force is applied to the rod 1366, as shown in FIG. 13A. When the rod 1366 is allowed to withdraw outward due to reduced pressure on the rod 1366, the spring 1350 may expand, thereby elongating the assembly 1360 and causing the chamber support structure (not shown) associated with the spring assembly 1360 to expand to provide compliance pressure in the target blood vessel, as shown in FIG. 13B.

In certain embodiments, the head portion 1360 may create a seal between the piston chamber 77 and the spring chamber 79. The head portion 1368 may comprise one or more nozzles to allow for fluid flow between the piston chamber 77 and the spring chamber 79, to thereby allow the piston head 1368 to move along a longitudinal axis of the assembly 1360. In certain embodiments, the head portion 1368 comprises two nozzles, wherein one of the nozzles 1367 is larger in diameter than the other nozzle 1369, such that more fluid may pass through the larger nozzle 1367 than the smaller nozzle 1369 when the piston head 1368 moves within the spring assembly 1360. In certain embodiments, the two nozzles may be the same size.

FIG. 13B illustrates the recovery phase of the spring assembly 1360. Because the flow of fluid from chamber to chamber is limited in one direction, when the spring is compressed or released, the speed of motion is limited by the flow of fluid through the open nozzle 1369.

In certain embodiments, one of the nozzles may comprise a check valve, such that fluid may move in one direction 1393, but not the opposite direction 1391. For example, one of the nozzles 1367 may be a check valve configured to allow fluid flow in the direction 1393 when the piston head moves in the opposite direction 1391, but to restrict fluid flow through the check valve 1367 when the piston head 1368 moves in the direction 1393 to expand the spring 1350. The check valve 1367 may comprise a ball check valve including a ball member 1362, or other closing member.

By utilizing a check valve as one of the nozzles, the diastolic energy release by the compliance restoration device may be drawn out over a longer period of time due to the restriction of expansion of the spring 1350, wherein the expansion of the spring 1350 is limited by the fluid flow through only the single open nozzle 1369. In certain embodiments, the check valve nozzle 1367 may be larger than the open nozzle 1369 to further increase the disparity between compression speed and expansion speed of the spring 1350. In certain embodiments, the open nozzle 1369 is relatively small in order to limit the speed of recovery of the spring 1350, wherein the check valve nozzle 1367 is at least partially closed during recovery.

Figure 14:
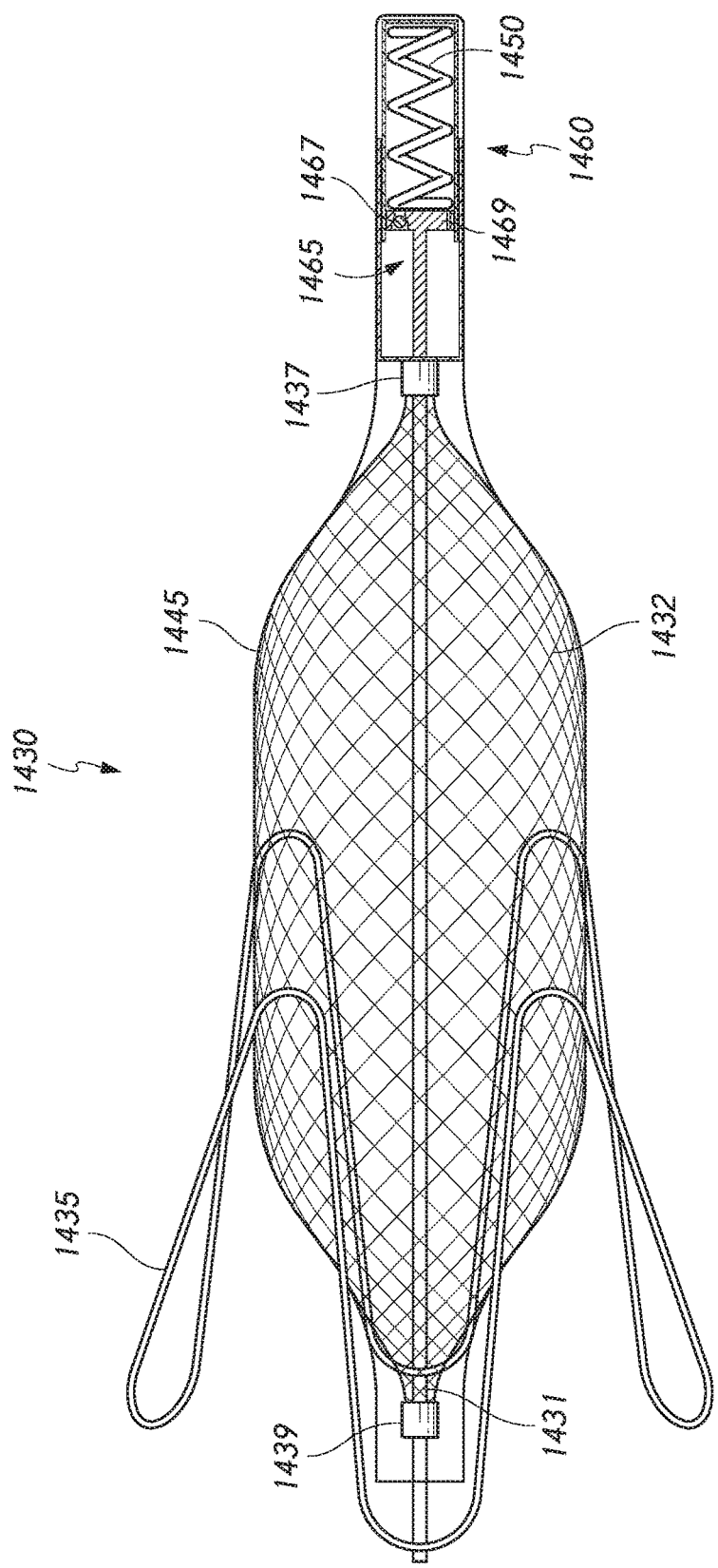
FIG. 14 illustrates a compliance restoration device including a viscoelastic spring assembly associated therewith according to one or more embodiments.

FIG. 14 illustrates a compliance restoration device 1430 including a viscoelastic spring assembly 1460 associated therewith to provide controlled recovery of the spring 1450 during diastole, as described above in connection with FIG. 13.

Figure 15:
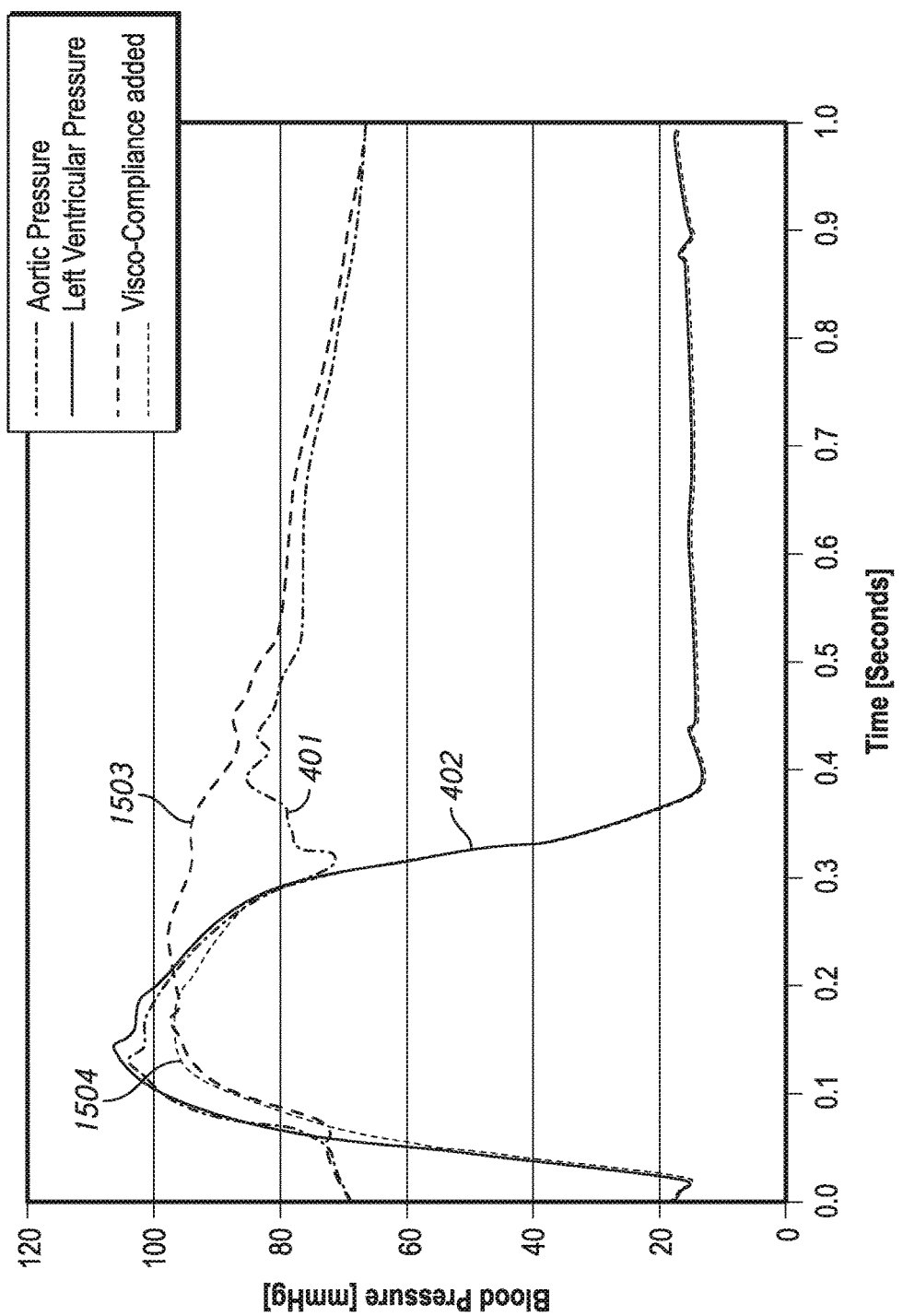
FIG. 15 is a graph illustrating example pressure waves associated with an example patient having a compliance restoration device incorporating a viscoelastic spring assembly in accordance with one or more embodiments.

FIG. 15 is a graph illustrating example pressure waves associated with the left ventricle and the aorta of an example patient having a compliance restoration device incorporating a viscoelastic spring assembly in accordance with one or more embodiments disclosed herein. The waveforms of FIG. 15 illustrate that the cyclic blood pressure may be relatively more smoothed and the diastolic pressure may be slightly lower, but longer lasting, for a compliance restoration device incorporating a viscoelastic spring assembly in accordance with one or more embodiments. Such performance/behavior may be particularly desirable for patients with diastolic heart failure.

Figure 16:
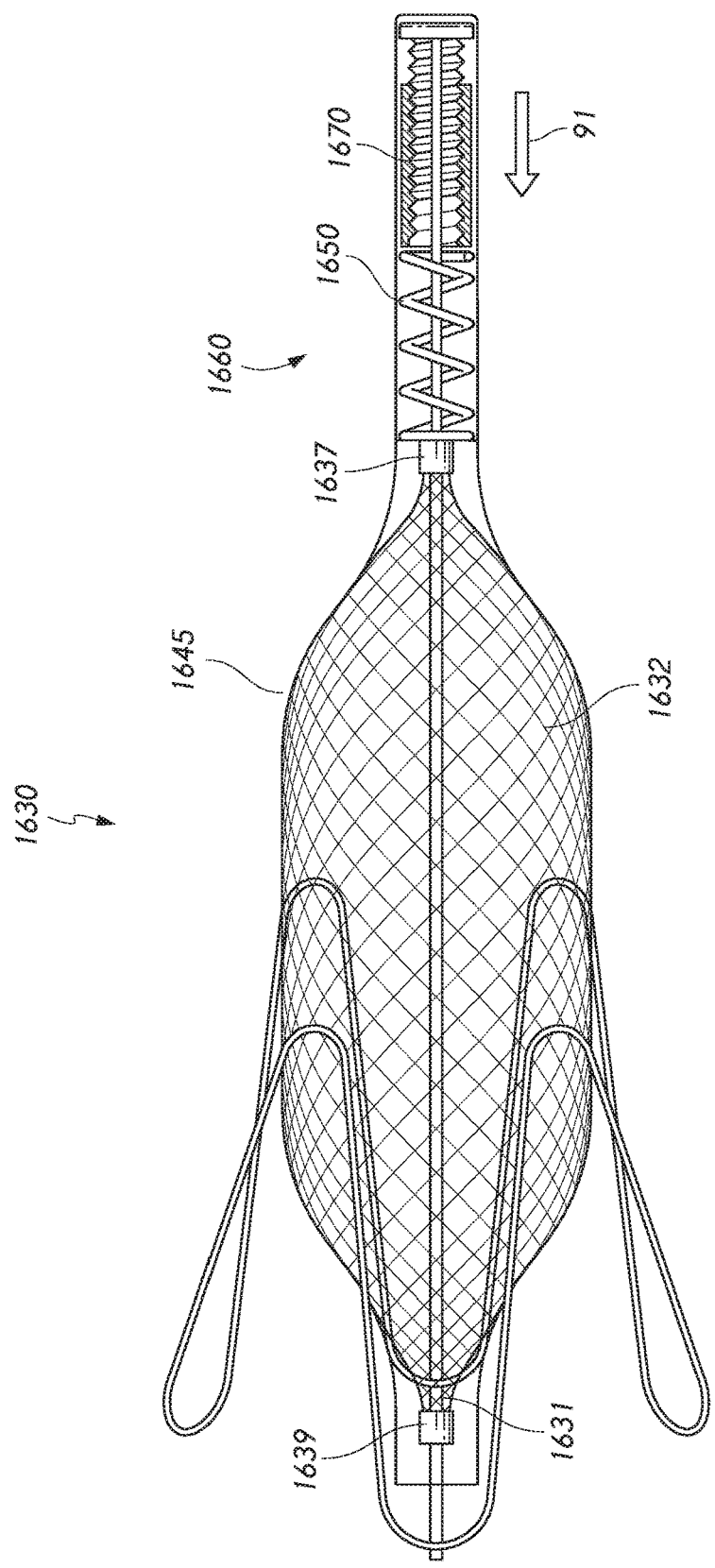
FIG. 16 illustrates a compliance restoration device having a tuned spring assembly in accordance with one or more embodiments.

FIG. 16 illustrates a compliance restoration device 1630 having a tuned spring assembly 1660. The tuned spring assembly 1660 may allow for the compliance restoration device 1630 to be tuned in accordance with specific patient conditions at the time of deployment. The tuned spring assembly 1660 comprises a spring 1650 mounted on a tuning screw 1670 that allows the implanting physician to set the preload on the spring 1650 at the time of implantation, and to optimize compliance to the patient condition. The tuning screw 1670 may have any suitable or desirable configuration and/or form. The tuning screw 1670 may be configured to exhort a fixed force in the direction 91 towards a distal end of the device 1630 in order to create compressive force on the spring 1650.

Elongated Compliance Device

Figure 17:
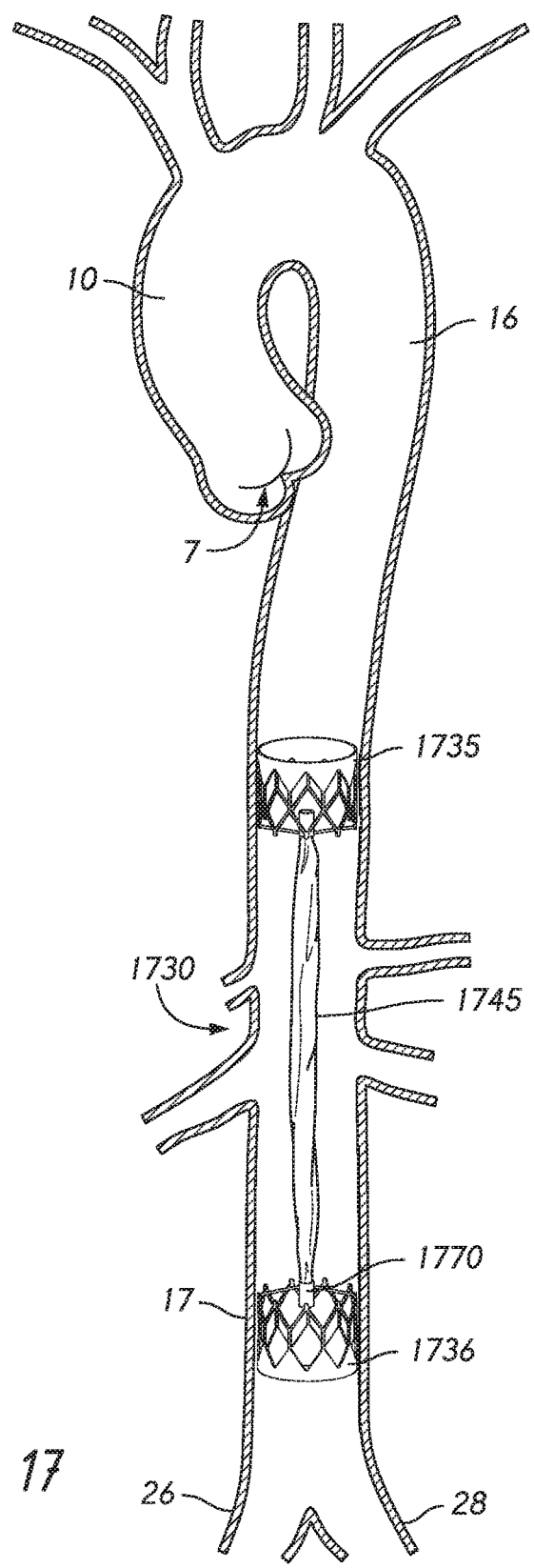
FIG. 17 illustrates a compliance restoration device implanted in an aorta in accordance with one or more embodiments.

FIG. 17 illustrates a compliance restoration device 1730 implanted in an aorta, such as in an abdominal region 17 of the aorta. The compliance restoration device 1730 may comprise two anchors, including a proximal anchor 1736 and a distal anchor 1735, wherein an elongated compliance balloon 1745 is connected between the two anchors.

In certain embodiments, the balloon 1745 is a compliant gas-charged balloon, which may provide an elastic, or flexible, balloon having a working volume between 10-40 ml. $CO_2$ gas, or other gas safe for human/device interaction may advantageously be utilized. The balloon 1745 may be axially placed in the descending aorta, and may be initially charged to match the patient's diastolic aortic pressure at rest.

In certain embodiments, fluoroscopic visualization of the balloon 1745 may be implemented, and balloon pressure adjustments may be made such that the balloon volume is minimal at systolic pressure, and expands to the selected working volume during diastole. The balloon may advantageously comprise material that is at least partially compliant, or flexible, as well as non-thrombogenic, biocompatible, and/or durable. For example, compliance balloons according to the present disclosure may advantageously comprise material have at least a 20-year durability expectation. In certain embodiments, the balloon 1745 may be fit over a support structure to maintain axial alignment with the native aorta. Such a support element may comprise, for example, a tubular member, a stiff rod, and/or a memory metal frame.

The balloon 1745 may have a length of approximately 200 mm, or larger. However, it may be desirable for the balloon to be small enough in length and/or diameter to avoid clogging of the aorta, using gas at approximately 80 mmHg, for example.

The compliance restoration device 1770 may include a gas fill port 1770 such that the balloon can be pressurized after it is anchored in the target blood vessel. In certain embodiments, a pressure valve allows for gas pressurization of the balloon. In certain embodiments, the compliance restoration device 1730 is configured to be decoupled from the delivery system (not shown), which may include the pressurization charging tube. The anchors 1735, 1736 may be secured to respective ends of the balloon 1745. The anchors can comprise self-expanding memory metal or other structure.

Figure 18:
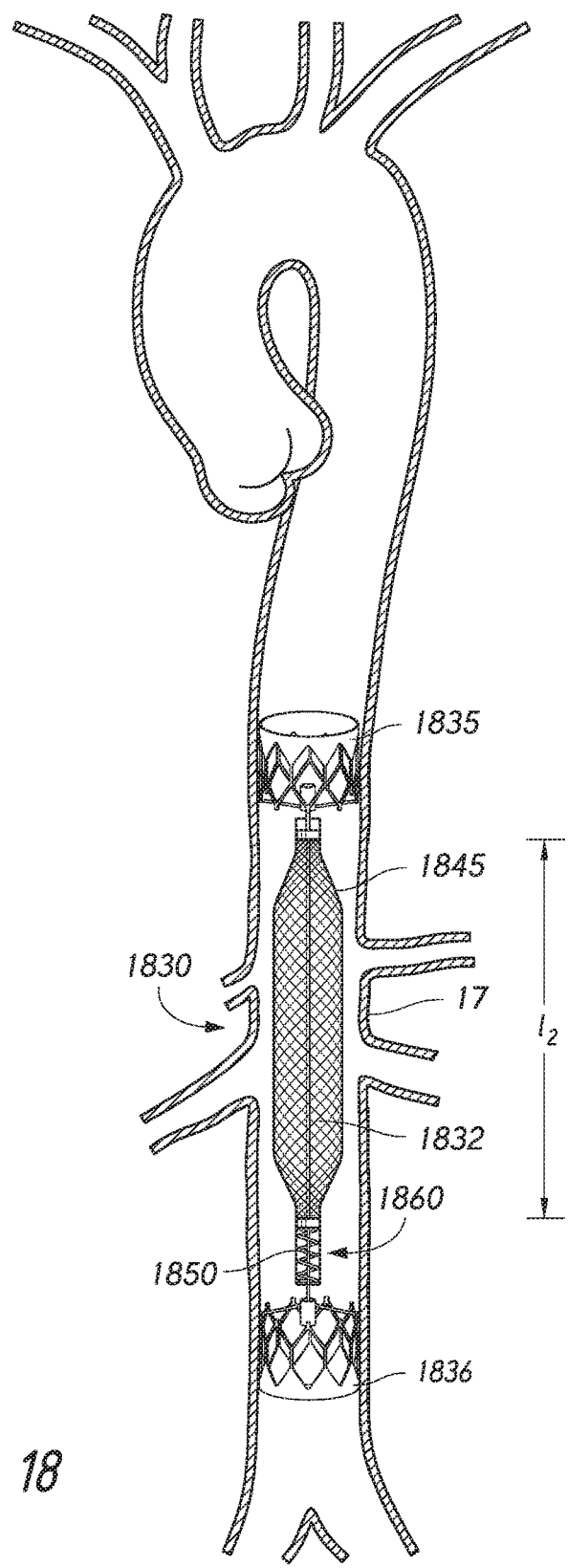
FIG. 18 illustrates a compliance restoration device implanted in an aorta in accordance with one or more embodiments.

FIG. 18 illustrates a compliance restoration device 1830 implanted in an aorta, such as in an abdominal region 17 of the aorta. The compliance restoration device 1830 may be similar in certain respects to the compliance restoration devices shown in FIG. 12E, FIG. 14, and/or FIG. 16, although the device 1830 of FIG. 18 may have different geometry and/or anchor(s) than certain other embodiments of compliance restoration devices described above.

The compliance restoration device 1830 may comprise a vacuum-filled compliance balloon 1845 that is supported by a chamber support structure 1832, which may be similar to other chamber support structures described herein and may comprise, for example, a wire mesh. The chamber support structure 1832 may be compressed at least in part by a spring assembly 1860 including a spring 1850. In certain embodiments, the compliance balloon 1845 may have a length $l_2$ of approximately 200 mm, between 150-200 mm, between 100-150 mm, between 50-100 mm, or some other value. In certain embodiments, the dimensions of the compliance balloon may affect resonant frequencies of pressure waves.

Chamber Support Forms

Figure 19:
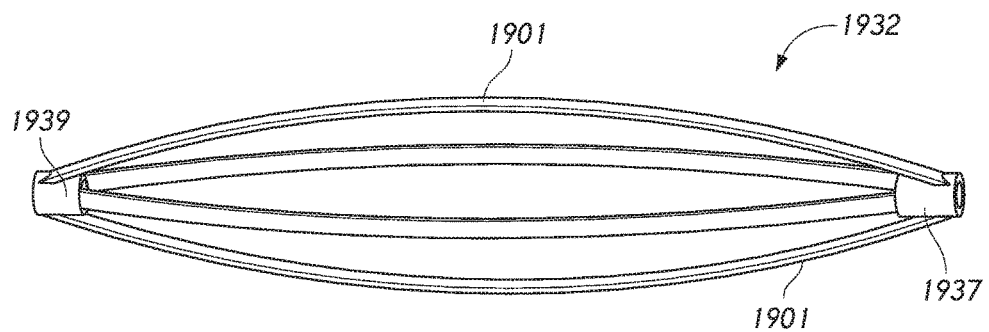
FIG. 19 shows a perspective view of a chamber support structure for a compliance restoration device in accordance with one or more embodiments.

FIG. 19 shows a perspective view of a chamber support structure 1932 for a compliance restoration device in accordance with one or more embodiments. The chamber support structure 1932 may comprise metal, plastic, and/or other at least partially rigid material. The chamber support structure may include one or more bands 1901 configured to at least partially bow or extend outward when first and second ends (1939, 1937) of the support structure 1932 are moved towards one another along a longitudinal axis of the support structure 1932. In certain embodiments, the bands 1901 may be generally concave, and may serve to expand to a diameter associated with a desired compliance restoration volume, and may provide support to a vacuum-sealed balloon disposed at least partially around the structure 1932, as described in detail herein. In certain embodiments, the bands 1901 are at least partially integrated with the end portions 1937, 1939. The bands 1901 may be configured to expand/bow-out without the formation of creases therein, thus presenting a generally continuous concavity, as illustrated.

Figure 20:
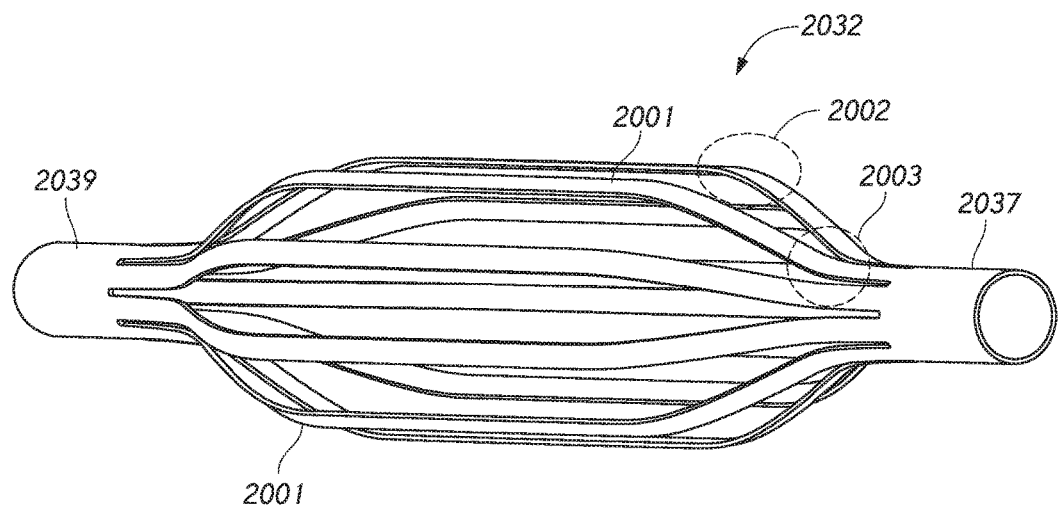
FIG. 20 shows a perspective view of a chamber support structure for a compliance restoration device in accordance with one or more embodiments.

FIG. 20 shows a perspective view of a chamber support structure for a compliance restoration device in accordance with one or more embodiments. The chamber support structure 2032 may comprise metal, plastic, and/or other at least partially rigid material. The chamber support structure may include one or more bands 2001 configured to at least partially bow or extend outward when first and second ends (2039, 2037) of the support structure 2032 are moved towards one another along a longitudinal axis of the support structure 2032. In certain embodiments, the bands 2001 may be generally concave, and may serve to expand to a diameter associated with a desired compliance restoration volume, and may provide support to a vacuum-sealed balloon disposed at least partially around the structure 2032, as described in detail herein. In certain embodiments, the bands 2001 are at least partially integrated with the end portions 2037, 2039. The bands 2001 may have one or more creases (2003, 2003) therein to allow for conformation of the expanded shape of the structure 2032 to a generally ellipsoidal shape, or other type of shape.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. A compliance restoration device comprising:
   a compliance balloon lumen;
   a chamber support structure disposed in the compliance balloon lumen and configured to expand to support an expanded volume of the compliance balloon lumen; and
   a spring assembly configured to cause the chamber support structure to expand by applying a force on a first end of the chamber support structure.

2. The compliance restoration device of claim 1, wherein the chamber support structure comprises a wire mesh form configured to expand outward when a distance between first and second ends of the wire mesh form decreases.

3. The compliance restoration device of claim 1, wherein the spring assembly comprises a one-way viscoelastic spring assembly.

4. The compliance restoration device of claim 3, wherein one-way the viscoelastic spring assembly comprises a piston component having first and second nozzles in a head portion of the piston component.

5. The compliance restoration device of claim 4, wherein the first nozzle comprises a check valve configured to allow fluid therethrough when a spring of the one-way viscoelastic spring assembly compresses and at least partially inhibit fluid flow therethrough when the spring expands.

6. The compliance restoration device of claim 1, wherein the spring assembly comprises a tuning screw.

7. The compliance restoration device of claim 1, wherein the compliance balloon lumen is configured to be vacuum sealed using a delivery catheter.

8. The compliance restoration device of claim 1, further comprising a first anchor structure.

9. The compliance restoration device of claim 8, wherein the first anchor structure is a wire-form anchor.

10. The compliance restoration device of claim 8, further comprising a second anchor structure coupled to a second end of the compliance balloon lumen, the first anchor structure being coupled to a first end of the compliance balloon lumen.

11. The compliance restoration device of claim 1, wherein the compliance restoration device is at least partially collapsible for delivery to a target blood vessel via a catheter delivery system through a minimally-invasive access port.

12. The compliance restoration device of claim 1, further comprising a central spine structure disposed at least partially within the chamber support structure and is coupled to first and second ends thereof.

* * * * *